United States Patent
Okamoto

(10) Patent No.: US 9,562,657 B2
(45) Date of Patent: Feb. 7, 2017

(54) LINE LIGHT IRRADIATION DEVICE

(71) Applicant: CCS INC., Kyoto-shi, Kyoto (JP)

(72) Inventor: Daisuke Okamoto, Kyoto (JP)

(73) Assignee: CCS INC., Kyoto (JP)

( * ) Notice: Subject to any disclaimer, the term of this patent is extended or adjusted under 35 U.S.C. 154(b) by 0 days.

(21) Appl. No.: 14/651,944

(22) PCT Filed: Dec. 17, 2013

(86) PCT No.: PCT/JP2013/083709
§ 371 (c)(1),
(2) Date: Jun. 12, 2015

(87) PCT Pub. No.: WO2014/098061
PCT Pub. Date: Jun. 26, 2014

(65) Prior Publication Data
US 2015/0345718 A1 Dec. 3, 2015

(30) Foreign Application Priority Data

Dec. 20, 2012 (JP) ................................. 2012-277808
Dec. 20, 2012 (JP) ................................. 2012-277809

(51) Int. Cl.
*F21S 4/00* (2016.01)
*F21V 19/00* (2006.01)
(Continued)

(52) U.S. Cl.
CPC .. *F21S 4/00* (2013.01); *F21S 4/28* (2016.01); *F21V 19/0035* (2013.01);
(Continued)

(58) Field of Classification Search
CPC ...... F21V 19/04; F21V 19/0085; F21V 23/06; F21S 4/28; F21S 4/00
See application file for complete search history.

(56) References Cited

U.S. PATENT DOCUMENTS

| 2005/0190553 A1 | 9/2005 | Lynch et al. |
| 2012/0020109 A1 | 1/2012 | Kim et al. |
| 2012/0243227 A1 | 9/2012 | Shimizu et al. |

FOREIGN PATENT DOCUMENTS

| DE | 102011008898 A1 | 7/2012 |
| DE | 202011051094 U1 | 11/2012 |

(Continued)

OTHER PUBLICATIONS

Apr. 8, 2014 Written Opinion issued in International Patent Application No. PCT/JP2013/083709.
(Continued)

*Primary Examiner* — David V Bruce
(74) *Attorney, Agent, or Firm* — Oliff PLC

(57) ABSTRACT

A line light irradiation device includes a plurality of light source units on which a plurality of light source mounting substrates are juxtaposed on a base in a row, and the plurality of light source units are juxtaposed in a row. The plurality of light source mounting substrates are positioned and fixed to the base at predetermined intervals. Thus, if a light source in a certain light source unit becomes defective, this light source unit can be removed so as to exchange only the light source mounting substrate on which the defective light source is mounted. Therefore, the normal light sources can be left as they are as much as possible, and waste of the light sources can be reduced. Further, the light source mounting substrates are positioned and fixed at predetermined intervals, and thus dimensional errors do not accumulate in the light source mounting substrates at the juxtaposition ends.

9 Claims, 17 Drawing Sheets

(51) Int. Cl.
*F21V 23/06* (2006.01)
*F21V 19/04* (2006.01)
*G01N 21/88* (2006.01)
*F21Y 101/00* (2016.01)

(52) U.S. Cl.
CPC ............ *F21V 19/042* (2013.01); *F21V 23/06* (2013.01); *G01N 21/8806* (2013.01); *F21Y 2101/00* (2013.01); *F21Y 2103/10* (2016.08); *F21Y 2115/10* (2016.08)

(56) References Cited

FOREIGN PATENT DOCUMENTS

| | | | |
|---|---|---|---|
| EP | 2489490 | A1 | 8/2012 |
| JP | 2005-302484 | A | 10/2005 |
| JP | 2006-275790 | A | 10/2006 |
| JP | 2009-117228 | A | 5/2009 |
| JP | 2009-288206 | A | 12/2009 |
| JP | 2011-113731 | A | 6/2011 |
| JP | 2012-028205 | A | 2/2012 |
| JP | 2012-064583 | A | 3/2012 |
| JP | 2012-204020 | A | 10/2012 |
| JP | 2012201020 | A * | 10/2012 |
| WO | 2005/024291 | A2 | 3/2005 |
| WO | 2011/139768 | A2 | 11/2011 |

OTHER PUBLICATIONS

Apr. 8, 2014 International Search Report issued in International Patent Application No. PCT/JP2013/083709.
Jul. 1, 2016 Extended European Search Report issued in European Patent Application No. 13863871.3.

* cited by examiner

LINE LIGHT IRRADIATION DEVICE

TECHNICAL FIELD

The present invention relates to a line light irradiation device that is capable of irradiating line-shaped light using a plurality of light sources such as LEDs.

BACKGROUND ART

Patent Literature 1 discloses one known example of such a line light irradiation device. This line light irradiation device includes a casing having a left-right pair of side panels and a bottom panel with an opening formed at the top panel side, and a light-emitting unit that is positioned on the bottom panel and has a plurality of LEDs (light sources) mounted in a row along the lengthwise direction on a long substrate.

In the light-emitting unit, the plurality of LEDs are mechanically mounted substantially linearly in one row so that their optical axes are aligned in a fixed direction on the surface of a strip-shaped printed circuit board. The LEDs are so-called power LEDs that can continuously pass a current of 200 mA or more, and are surface mounting-type LEDs in which LED elements are arranged in the center of a rectangular panel-shaped package. The LEDs are disposed, for example, such that the LED elements are aligned at fixed intervals in a single, substantially linear row.

Since a light source such as an LED light source has a useful life, the light source must be periodically exchanged, or exchanged every time a set number of usage hours have elapsed. Therefore, in the above-mentioned line light irradiation device, since each LED light source is fixed to a substrate within the device, when exchanging the LED light sources, the device had to be taken apart to remove the substrate and exchange each LED light source one-by-one or exchange the entire substrate.

However, there have been problems in that this kind of exchange operation required considerable time and labor and the operation efficiency was poor, and the manufacturing line had to be stopped for a long time when exchanging the LED light sources during manufacturing, which led to decreased productivity.

Patent Literature 2 discloses one known example of a line light irradiation device that solves the above-described problems.

This line light irradiation device includes a light source unit obtained by bonding a light source mounting substrate on which a plurality of light sources are mounted in a line shape and a heat radiation member that radiates heat from the light source mounting substrate, a main body housing on which a plurality of the light source units are aligned and mounted, and a drive control part that outputs a drive signal to the light source mounting substrate of each light source unit.

According to this kind of line light irradiation device, when a light source needs to be exchanged due to reaching the end of its life or the like, the light source units can be removed from the main body housing and each light source unit can be exchanged individually. Thus, the maintenance is easy and the operability is improved.

CITATION LIST

Patent Literature

Patent Literature 1: JP 2006-275790 A
Patent Literature 2: JP 2009-288206 A

SUMMARY OF INVENTION

Technical Problem

In the conventional line light irradiation device disclosed in Patent Literature 2, one long light source mounting substrate is provided to each light source unit, and a plurality of LEDs which serve as light sources are mounted linearly on the light source mounting substrate. Therefore, if a certain light source (LED light source) becomes defective due to reaching the end of its life or a malfunction, the entire long light source mounting substrate must be exchanged even though the other light sources are normal, and thus these other light sources will be wasted.

Therein, it would be conceivable to reduce waste of the light sources by dividing the long light source mounting substrate into a plurality of small light source mounting substrates and mounting a plurality of light sources on each small light source mounting substrate, so that only the light source mounting substrate containing the defective light source needs to be exchanged while the other light source mounting substrates containing normal light sources can be left as they are.

However, in this case, if the small light source mounting substrates are juxtaposed without any spaces therebetween, dimensional errors may accumulate in the light source mounting substrates at the juxtaposition ends due to dimensional errors in the manufacture of the light source mounting substrates. If such accumulation of dimensional errors occurs, there may be cases in which the distance between light source mounting substrates in between adjacent light source units increases or decreases more or lower than a predetermined tolerance. In such cases, illuminance unevenness may occur between adjacent light source units.

For example, as shown in FIG. 17A, if a plurality of light source mounting substrates 10 are juxtaposed in a row without any spaces therebetween on a light source unit K, dimensional errors will accumulate in the light source mounting substrates at the juxtaposition ends. If this occurs, the interval between the light source mounting substrates 10 and 10 positioned at the juxtaposition ends in the adjacent light source units K and K may become too large, and the radiation illuminance in this portion may fall below an allowable line, leading to the occurrence of illuminance unevenness.

The present invention was created in consideration of the above-described problems, and an object thereof is to provide a line light irradiation device in which waste of the light sources can be reduced and illuminance unevenness between adjacent light source units can be prevented when a light source mounting substrate must be exchanged due to a defect in a certain light source caused by the light source reaching the end of its life or malfunctioning.

Solution to Problem

To achieve the above object, a line light irradiation device of the present invention includes:
a light source mounting substrate on which a plurality of light sources are mounted in a row; and
a light source unit on which a plurality of the light source mounting substrates are provided on a base in a row direction of the light sources,
wherein a plurality of the light source units are juxtaposed in the row direction of the light sources, and
the plurality of light source mounting substrates are fixed with intervals therebetween to the base by fixation means.

In the present invention, a plurality of light source mounting substrates are fixed with intervals therebetween to the base by fixation means. Therefore, dimensional errors do not accumulate in the light source mounting substrates at the juxtaposition ends. Thus, the distance between light source mounting substrates in between adjacent light source units does not increase or decrease more or lower than a predetermined value, and this distance is kept within the predetermined tolerance. Accordingly, illuminance unevenness can be prevented between adjacent light source units.

For example, as shown in FIG. 17B, by fixing the light source mounting substrates 10 in a row with fixed intervals therebetween on each light source unit K, dimensional errors in the light source mounting substrates 10 do not accumulate in the light source mounting substrates 10 at the juxtaposition ends. Thus, the interval between the light source mounting substrates 10 and 10 positioned at the juxtaposition ends of adjacent light source units K and K does not become too large. Therefore, the radiation illuminance does not fall below an allowable line, and as a result the occurrence of illuminance unevenness can be prevented.

Further, if a certain light source in a certain light source unit becomes defective, this light source unit can be removed so as to exchange only the light source mounting substrate on which the defective light source is mounted, and it is not necessary to exchange the other light source mounting substrates on which normal light sources are mounted.

Therefore, the normal light sources can be left as they are as much as possible, and as a result, waste of the light sources can be reduced.

In the above-described structure of the present invention, the following is preferable:

the light source mounting substrates that are on both sides among the plurality of light source mounting substrates disposed on the base are positioned so as to leave a space toward the inside from the side surfaces of the base, and the plurality of light source units are juxtaposed in a state in which the side surfaces of the bases are abutted to each other, and thereby the light source mounting substrate positioned at the side surface of the base of one light source unit among two adjacent light source units and the light source mounting substrate positioned at the side surface of the base of the other light source unit are disposed with a predetermined interval therebetween.

With this structure, by abutting the light source units to each other, the light source mounting substrate positioned at the side surface of the base of one light source unit and the light source mounting substrate positioned at the side surface of the base of the other light source unit are disposed with a predetermined interval therebetween. Therefore, the occurrence of illuminance unevenness between the light source units can be easily and reliably prevented.

In the above-described structure of the present invention, the following is preferable:

the fixation means has a fixation part that supplies power to each light source mounting substrate disposed on the base and fixes the light source mounting substrate, and the fixation part has a fixation terminal that supplies power to the light source mounting substrate and compresses and fixes the light source mounting substrate to the base.

With this structure, the light source mounting substrate is fixed by compression onto the base by the fixation terminal, and thereby the light source mounting substrate that has been positioned can be fixed and power can be supplied to the light source mounting substrate.

In the above-described structure of the present invention, the following is preferable:

the fixation means has a disposal groove that is formed on the base and restricts movement of each light source mounting substrate disposed on the base in a direction orthogonal to a disposal direction of the light source mounting substrate.

With this structure, the light source mounting substrate can be positioned in a direction orthogonal to the disposal direction by the disposal groove.

In the above-described structure of the present invention, the following is preferable:

the fixation part has a float-up prevention part that abuts or approaches an upper surface edge of each light source mounting substrate and prevents the light source mounting substrate from floating up.

With this structure, the light source mounting substrates can be prevented from floating up by the float-up prevention part. Thus, the light source mounting substrates, which are expensive, can be prevented from deviating from the base and becoming damaged or broken even if a portion of the fixation terminal becomes broken during assembly or the like.

In the above-described structure of the present invention, the following is preferable:

the interval between the light source mounting substrate positioned at the side surface of the base among the plurality of light source mounting substrates disposed on the base and the side surface of the base is ½ of the interval between adjacent light source mounting substrates on the base.

With this structure, the distance between the light source mounting units positioned at opposing side surfaces of adjacent bases is equal to the interval between adjacent light source mounting substrates on the base. Therefore, in the line light irradiation device including a plurality of light source units, illuminance unevenness between adjacent light source mounting substrates can be prevented and light can be more uniformly irradiated.

In the above-described structure of the present invention, the following is preferable:

the fixation part is provided on both sides of the light source mounting substrates so as to form a pair of fixation parts sandwiching the light source mounting substrates, and each fixation part has a plurality of the fixation terminals, and one side of each of the plurality of light source mounting substrates is fixed to the base by the fixation terminals of one of the fixation parts, and the other side of each of the plurality of light source mounting substrates is fixed to the base by the fixation terminals of the other fixation part.

With this structure, both sides of the plurality of light source mounting substrates can be fixed to the base by the plurality of fixation terminals of the pair of fixation parts, and thus the plurality of light source mounting substrates can be reliably fixed to the base.

In the above-described structure of the present invention, the following is preferable:

the fixation part has a restriction part that abuts the side surface of each light source mounting substrate to restrict movement of the light source mounting substrate in the disposal direction of the light source mounting substrate.

With this structure, the light source mounting substrate can be positioned in the disposal direction by abutting the restriction part to the side surface of the light source mounting substrate.

In the above-described structure of the present invention, the following is preferable:

a protrusion is formed on one of the fixation part or the base, and a recess with which the protrusion engages is formed on the other of the fixation part or the base, and the fixation part engages with the base in a protrusion-recess manner via the protrusion and recess.

With this structure, the fixation part engages with the base in a protrusion-recess manner via the protrusion and recess. Therefore, when fixing the plurality of light source mounting substrates by the fixation part or the like, the fixation part can be prevented from rotating in a plane parallel to the light source mounting substrates. Thus, the fixation part can be prevented from rotating and hitting the light source mounting substrates and in turn scratching the light source mounting substrates or causing them to deviate from the base.

Advantageous Effects of Invention

According to the present invention, if a certain light source becomes defective due to reaching the end of its life or a malfunction, the normal light sources can be left as they are, and thus waste of the light sources can be reduced and the occurrence of illuminance unevenness between adjacent light source units can be prevented.

BRIEF DESCRIPTION OF DRAWINGS

FIG. 1(a) is a perspective view and FIG. 1 (b) is an exploded perspective view.

DESCRIPTION OF EMBODIMENTS

Figure 1:
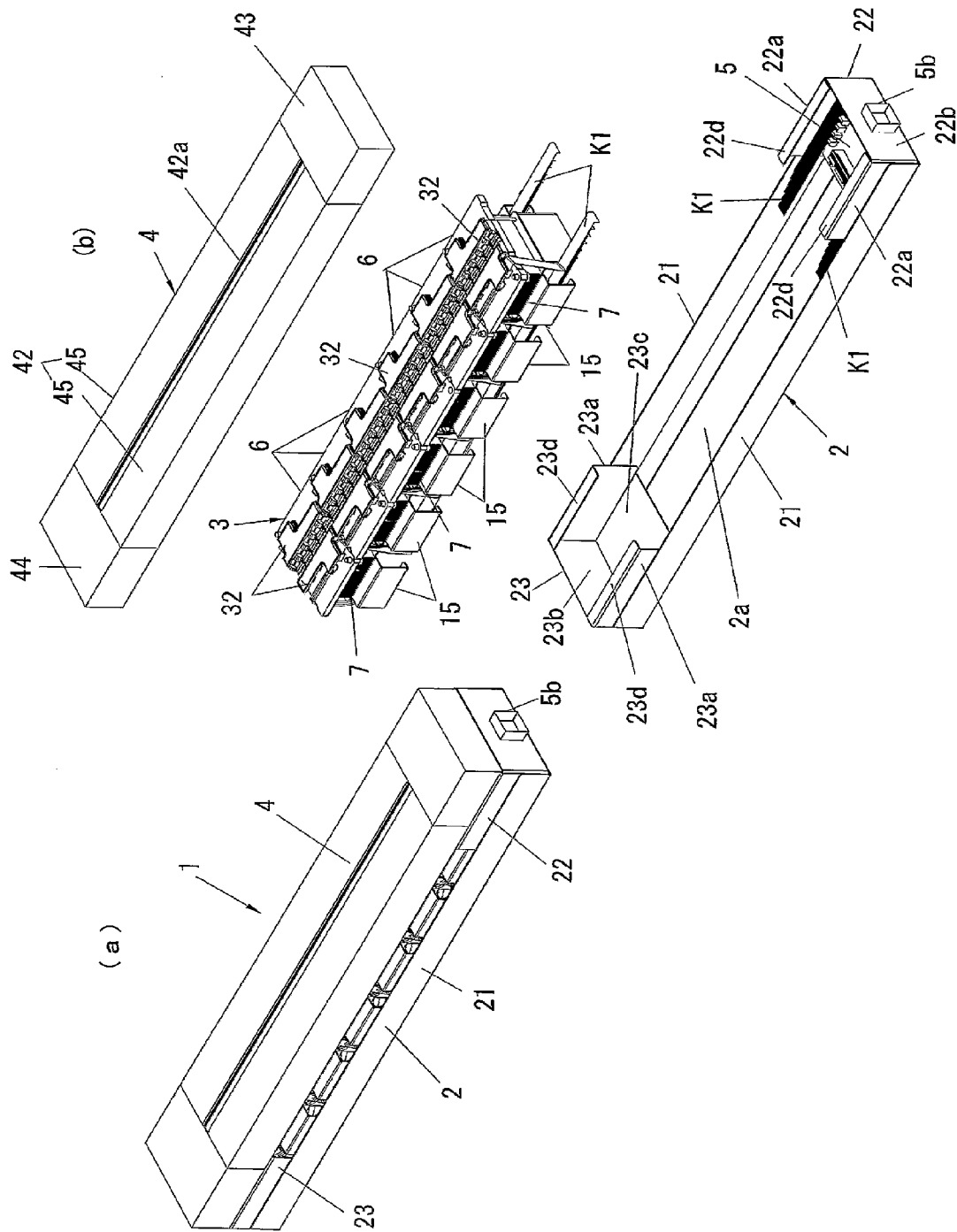
FIG. 1 illustrates a line light irradiation device according to an embodiment of the present invention.

Embodiments of the present invention will now be explained below referring to the drawings.

FIG. 1 illustrates a line light irradiation device according to an embodiment of the present invention, and FIG. 1(a) is a perspective view and FIG. 1(b) is an exploded perspective view.

As shown in FIG. 1, a line light irradiation device 1 has a casing 2 that serves as an outer packaging, a light source unit aggregate 3 that is accommodated in the casing 2, and a lens unit 4 that is placed on the casing 2.

The line light irradiation device 1 of the present embodiment irradiates ultraviolet radiation, and is used to, for example, cure a photocurable resin with the ultraviolet radiation.

The casing 2 has a substantially rectangular parallelepiped shape formed by metal, and is constituted by side frames 21 and 21 that have an L-shaped cross section and are disposed opposing each other front-to-back and spaced apart from each other in parallel, and end frames 22 and 23 that are attached to both ends of the side frames 21 and 21 and connect the side frames 21 and 21.

In FIG. 1, the long dimension direction of the casing 2 is referred to as the left-right direction, and the short dimension direction is referred to as the front-back direction.

One piece of each side frame 21 having an L-shaped cross section constitutes a side panel of the casing 2, and the other piece constitutes a bottom panel of the casing 2. An opening 2a having a long rectangular shape extending left-to-right is provided in the bottom of the casing 2. An air intake inlet of a blower fan 8 to be explained later is configured to face the opening 2a.

The end frame 22 plugs one end opening between the side frames 21 and 21, and a control substrate 5 is provided inside the end frame 22. The end frame 22 has side panels 22a and 22a that have an L-shaped cross section and are disposed opposing each other front-to-back and spaced apart from each other in parallel, and an end panel 22b and a bottom panel (not illustrated) that connect the side panels 22a and 22a to each other. Receiving surfaces 22d that receive the lens unit 4 are formed on the top ends of the side panels 22a. The side panels 22a are taller than the side frames 21, and thereby the receiving surfaces 22d are positioned higher than the side frames 21.

The side panels 22a and 22a are abutted and fixed to the inner surfaces of the side frames 21 and 21, and thereby the end frame 22 is fixed to the side frames 21 and 21.

The end frame 23 plugs the other end opening between the side frames 21 and 21. The end frame 23 has side panels 23a and 23a that have an L-shaped cross section and are disposed opposing each other front-to-back and spaced apart from each other in parallel, and an end panel 23b and a bottom panel 23c that connect the side panels 23a and 23a to each other. Receiving surfaces 23d that receive the lens unit 4 are formed on the top ends of the side panels 23a. The side panels 23a are taller than the side frames 21, and thereby the receiving surfaces 23d are positioned higher than the end frames 22.

The side panels 23a and 23a are abutted and fixed to the inner surfaces of the side frames 21 and 21, and thereby the end frame 23 is fixed to the side frames 21 and 21.

The light source unit aggregate 3 is constituted by juxtaposing a plurality (for example, six) of light source units 6 in a row left-to-right.

Figure 2:
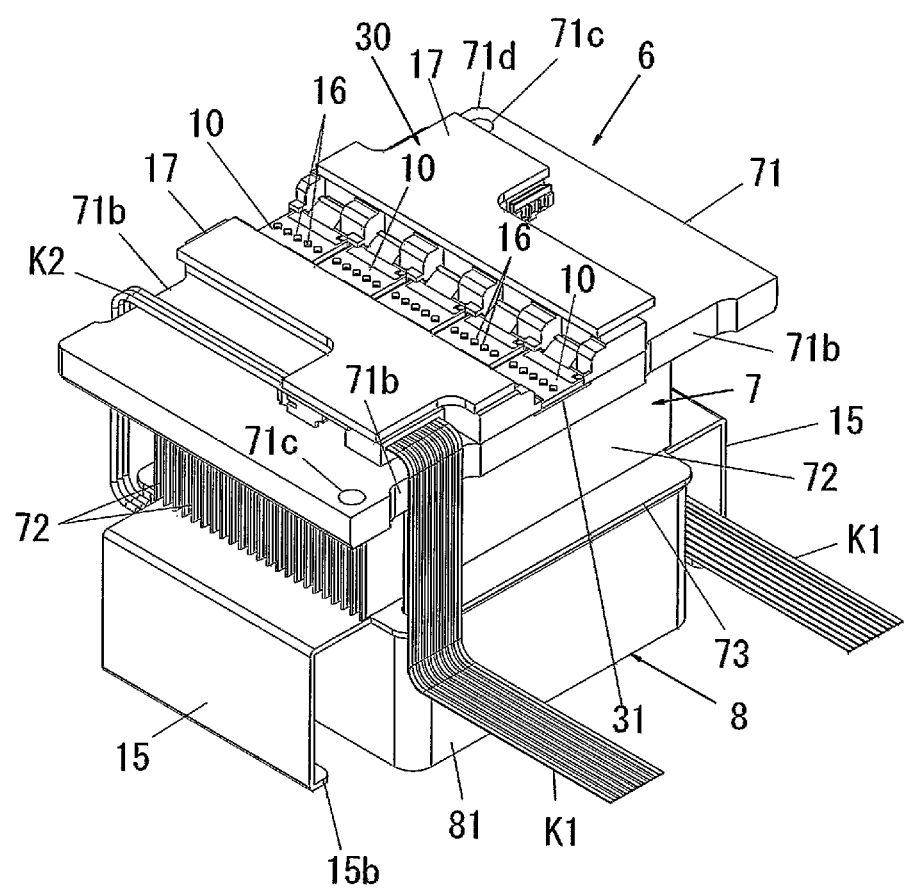
FIG. 2 is a perspective view of a light source unit.
Figure 3:
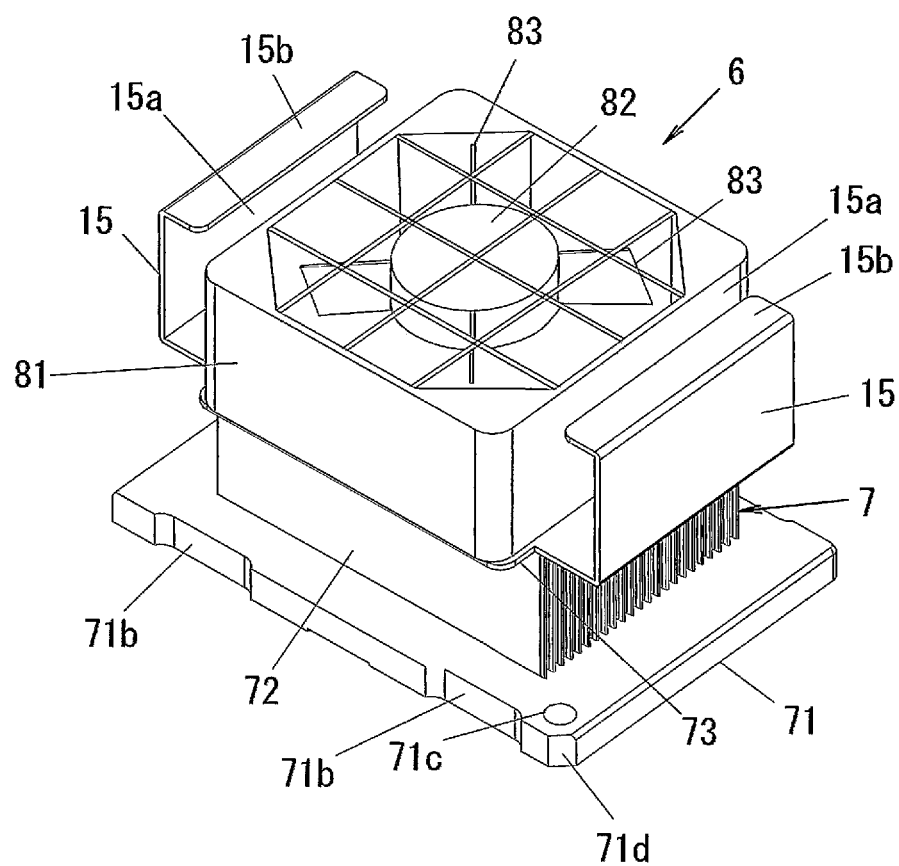
FIG. 3 is a perspective view illustrating a state in which a blower fan is attached to a heat sink.

As shown in FIGS. 2 and 3, each light source unit 6 has a heat sink 7, a blower fan 8 provided on the bottom surface of the heat sink 7, and a plurality (for example, five) of light source mounting substrates 10 provided on the top surface of the heat sink 7.

The heat sink 7 is made of metal, and has a base 71 formed in a rectangular panel shape, multiple fins 72 formed on the bottom surface of the base 71, and a flat panel 73 that is provided on the bottom end of the multiple fins 72 and abuts the blower fan 8.

Figure 4:
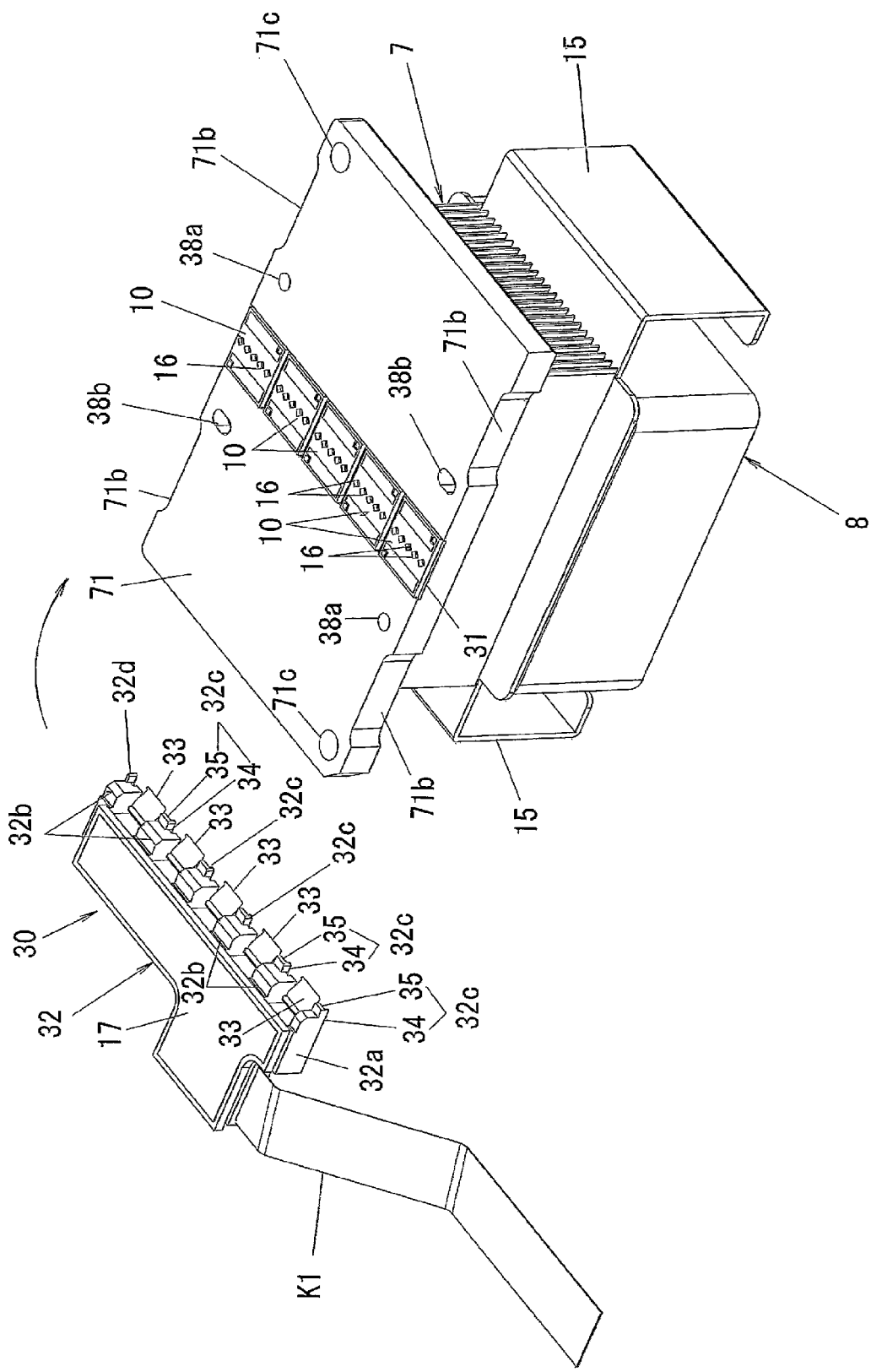
FIG. 4 is a perspective view illustrating a heat sink and a fixation part.

As shown in FIG. 4, a disposal groove 31 to be explained later is formed on the top surface of the base 71. Recess-shaped cut-away portions (passing portions) 71b and 71b are formed spaced apart from each other on the side surfaces along the longer dimension direction of the base 71 in order to allow power supply cables K1 and K2 to be explained later to pass therethrough. A chamfered part 71d is formed on one of the four corners of the base 71.

As shown in FIG. 2, the multiple fins 72 are disposed so that their surfaces are parallel to the longer dimension direction of the base 71 and oppose the shorter dimension direction of the base 71 with a predetermined interval therebetween.

The flat panel 73 is formed in a rectangular shape and is thinner than the base 71, and the flat panel 73 is disposed parallel to the base 71 sandwiching the fins 72 therebetween.

A case 81 of the blower fan 8 is abutted to the bottom surface of the flat panel 73. A circular hole (not illustrates) for sending air from the blower fan 8 to the fins 72 is formed in approximately the center of the flat panel 73.

The flat panel 73 and the case 81 of the blower fan 8 are attached to the base 71 sandwiching the multiple fins 72 therebetween, and the base 71, the fins 72, the flat panel 73, and the case 81 are connected integrally.

The blower fan 8 is for blowing air on the heat sink 7, and has the case 81, a motor 82 provided within the case 81, and a plurality of fans 83 attached to a drive shaft of the motor 82.

The blower fan 8 is disposed on the inside of the base 71 of the heat sink 7 in a plan view in the juxtaposition direction of the light source units 6 (the shorter dimension direction of the base 71 in FIG. 2) and in the direction orthogonal to the juxtaposition direction of the light source units 6 (the longer dimension direction of the base 71 in FIG. 2).

The blower fan 8 takes in outside air from the bottom surface thereof and blows out the air from the top surface thereof toward the fins 72 through the circular hole (not illustrated) formed in the flat panel 73.

The air which has been blown out absorbs the heat of the fins 72 through the surfaces of the fins 72 and is then blown out from the side surfaces of the heat sink 7. The heat from the base 71 is conducted into the fins 72.

As shown in FIG. 2, etc., insertion parts 15 and 15 through which the cable K1 to be explained later is passed are provided avoiding the sides of the fins 72 on opposing sides of the heat sink 7 on the underside of the base 71. Each insertion part 15 is constituted by a panel having a substantially L-shaped cross-section that is formed integrally with the flat panel 73, and each insertion part 15 is formed opposing and spaced apart from the side surface of the blower fan 8 so as to project from the side of the heat sink 7.

Each insertion part 15 is configured such that the cable K1 is inserted into a space inside the panel having an L-shaped cross-section (the space between the panel having an L-shaped cross-section and the side surface of the blower fan 8). Each insertion part 15 has an insertion opening 15a for inserting the cable K1 into the insertion part 15 from a direction intersecting the lengthwise direction of the cable K1. A bent piece 15b obtained by bending the distal edge of the panel having an L-shaped cross-section toward the inside is formed on the lower end of each insertion part 15. The bent piece 15b constitutes a deviation prevention part 15b that prevents deviation of the cable K1 that is inserted into the insertion part 15.

As shown in FIG. 2 and FIGS. 4 to 6B, a plurality (for example, five) of the light source mounting substrates 10 are juxtaposed in a row in the left-right direction (the shorter dimension direction of the base 71) on the base 71 of the light source unit 6, and a plurality (for example, five) of light sources 16 are mounted in a row in the left-right direction on each light source mounting substrate 10.

In the present embodiment, the light sources 16 are ultraviolet LED light sources. However, the light sources 16 are not limited thereto, and infrared LED light sources and visible light sources may also be used. Further, a light source other than an LED light source may also be used.

The plurality of light source mounting substrates 10 are positioned and fixed on the base 71 with predetermined intervals therebetween in the disposal direction of the light source mounting substrates 10 (the shorter dimension direction of the base 71) by positioning/fixation means (fixation means) 30.

An interval X between adjacent light source mounting substrates 10 and 10 is set to, for example, 0.5 mm≤X≤2.0 mm, preferably to 0.8 mm≤X≤1.5 mm, and more preferably to 0.9 mm≤X≤1.1 mm.

By setting the interval between adjacent light source mounting substrates 10 and 10 as described above, the occurrence of illuminance unevenness between the light source mounting substrates 10 and 10 can be prevented.

An interval between the light source mounting substrate 10 positioned at the side surface of the base 71 among the plurality of light source mounting substrates 10 disposed on the base 71 and the side surface of the base 71 is set to ½ of the interval between adjacent light source mounting substrates 10 and 10 on the base 71.

Figure 6A:
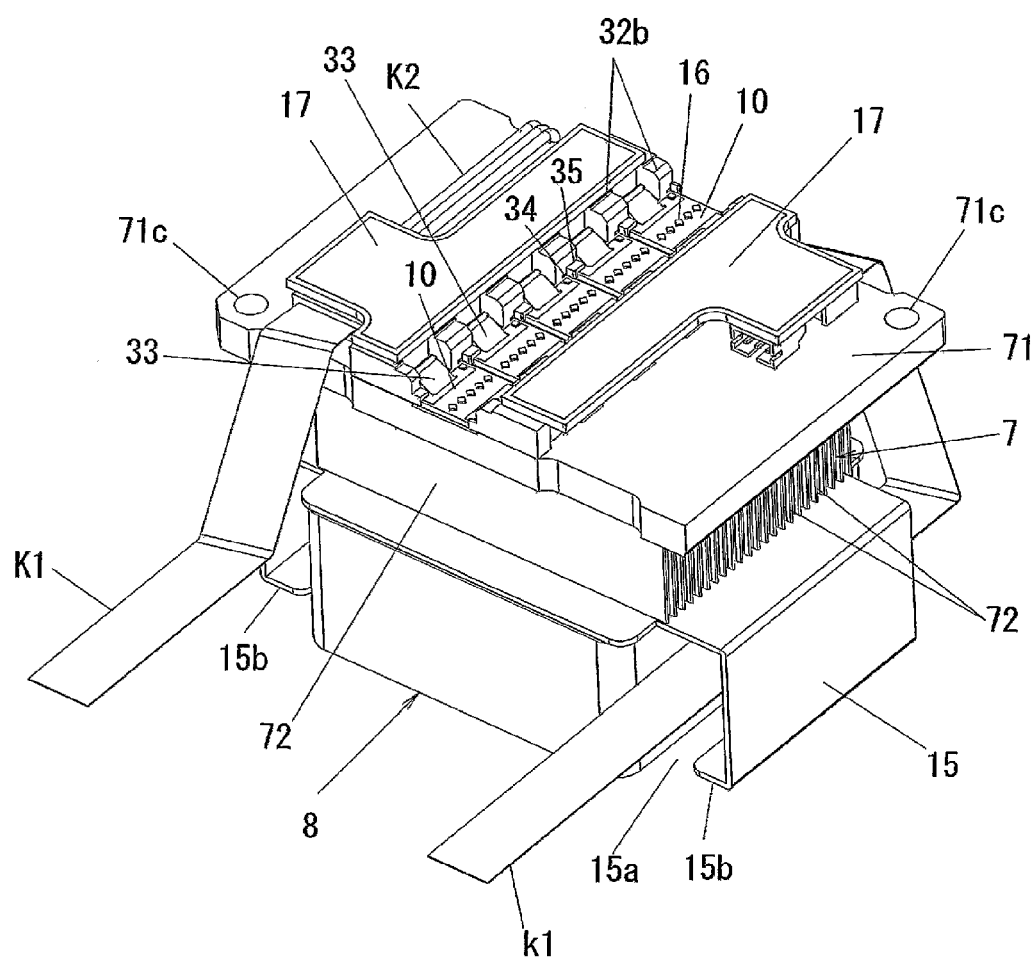
FIG. 6A is a perspective view illustrating a state in which the light source mounting substrates disposed on a base of the heat sink are pressed by both fixation parts.
Figure 6B:
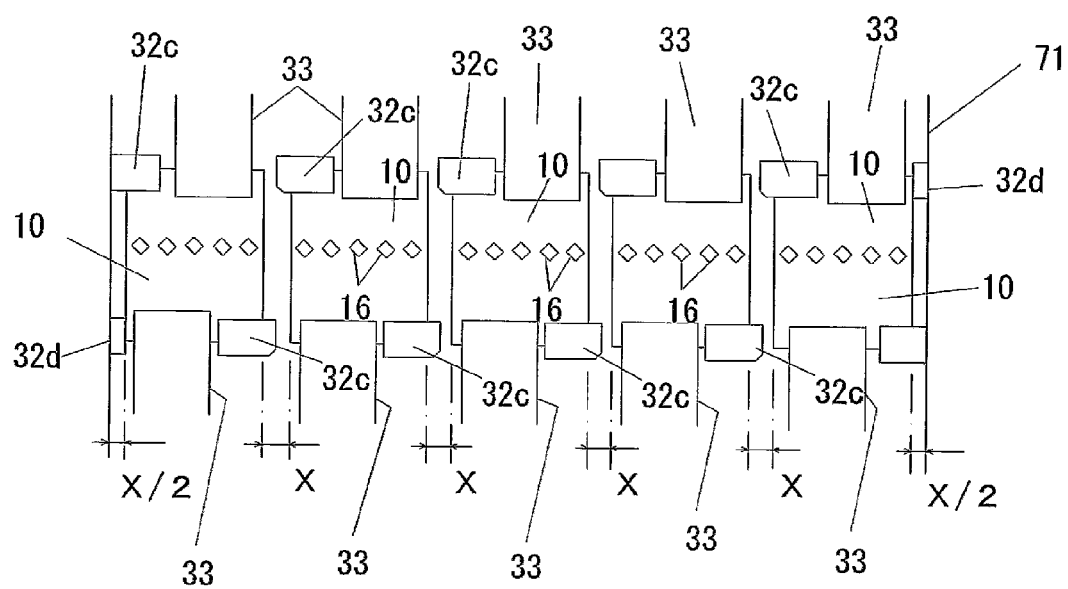
FIG. 6B is a plan view illustrating an arrangement state of the light source mounting substrates.

In other words, as shown in FIG. 6B, if the interval between adjacent light source mounting substrates 10 and 10 on the base 71 is X, then the interval between the light source mounting substrate 10 positioned at the side surface of the base 71 and the side surface is X/2.

The positioning/fixation means 30 also positions and fixes the light source mounting substrates 10 in a direction orthogonal to the disposal direction of the light source mounting substrates (the longer dimension direction of the base 71).

The positioning/fixation means 30 is constituted by a disposal groove 31 formed on the base 71 and a fixation part 32 provided on the base 71.

As shown in FIGS. 2 and 4, the disposal groove 31 is formed in the center in the longer dimension direction of the top surface of the base 71 so as to extend in the shorter dimension direction of the base 71 from one side surface along the longer dimension direction of the base 71 to the other side surface. The groove width of the disposal groove 31 is nearly equal to or slightly larger than the width of the light source mounting substrates 10.

Therefore, by inserting and disposing the light source mounting substrates 10 into the disposal groove 31 so that the width direction of the light source mounting substrates 10 is oriented toward the width direction of the disposal groove 31, the light source mounting substrates 10 are positioned so that any movement of the light source mounting substrates 10 in a direction orthogonal to their disposal direction (the longer dimension direction of the base 71) is restricted.

The depth of the disposal groove 31 is slightly shallower than the thickness of the light source mounting substrates 10. Thereby, the top surface of each light source mounting substrate 10 disposed in the disposal groove 31 protrudes slightly from the top surface of the base 71.

The fixation part 32 supplies power to the light source mounting substrates 10 disposed in the disposal groove 31, and fixes the light source mounting substrates 10 at predetermined intervals in the shorter dimension direction of the base 71 (the lengthwise direction of the disposal groove 31). A pair of fixation parts 32 is provided so as to sandwich the disposal groove 31.

Each fixation part 32 has fixation terminals 33, restriction parts 34, and float-up prevention parts 35. The fixation terminals 33 supply power to the light source mounting substrates 10 and compress and fix the light source mounting substrates 10 to the bottom surface of the disposal groove 31. A plurality (for example, five) of the fixation terminals 33 are provided at predetermined intervals in the juxtaposition direction of the light source mounting substrates 10.

The number of fixation terminals 33 that are provided is the same as the number of light source mounting substrates 10, and one edge of each light source mounting substrate 10 is compressed from above by one fixation terminal 33. Each fixation terminal 33 is shaped into a thin panel, and the distal edge of each fixation terminal 33 elastically contacts the light source mounting substrate 10. Thereby, the light source mounting substrate 10 is compressed and power is supplied to the light source mounting substrate 10.

In the case that the light source mounting substrates 10 are formed by, for example, a ceramic substrate, the light source mounting substrates 10 cannot be fixed to the base 71 by screwing or soldering or the like. However, in the present embodiment, the light source mounting substrates 10 are fixed by the fixation terminals 33, and thus the light source mounting substrates 10 can be easily and reliably fixed to the base 71.

A relay substrate 17 is attached to the top surface of each fixation part 32, and the fixation terminals 33 are electrically connected to the relay substrate 17. A cable K1 for supplying power to the fixation terminals 33 and transmitting control signals is connected to each relay substrate 17.

Each cable K1 is constituted by a flexible flat cable (FFC). A cable K2 that supplies power to the blower fan 8 and transmits control signals is also connected to the relay substrate 17. The cable K2 extends from the blower fan 8 and crawls to the top surface side of the base 71 through the cut-away portion 71b of the base 71, and then connects to the relay substrate 17. The cable K2 is a normal wire-shaped cable, but a flexible flat cable (FFC) can also be used.

The restriction parts 34 abut the side surfaces of the light source mounting substrates 10 to restrict the movement of the light source mounting substrates 10 in the lengthwise direction of the disposal groove 31. Each restriction part 34 is configured as described below.

Figure 5A:
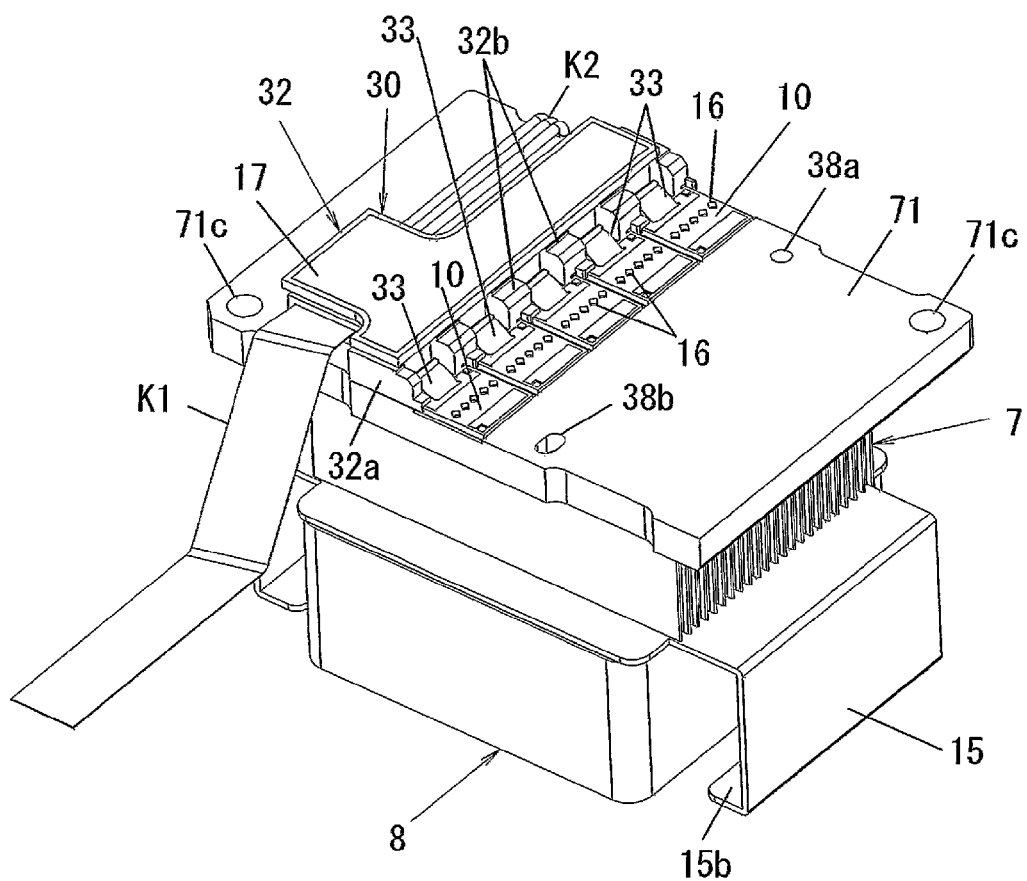
FIG. 5A is a perspective view illustrating a state in which light source mounting substrates disposed on abase of the heat sink are pressed by one fixation part.
Figure 5B:
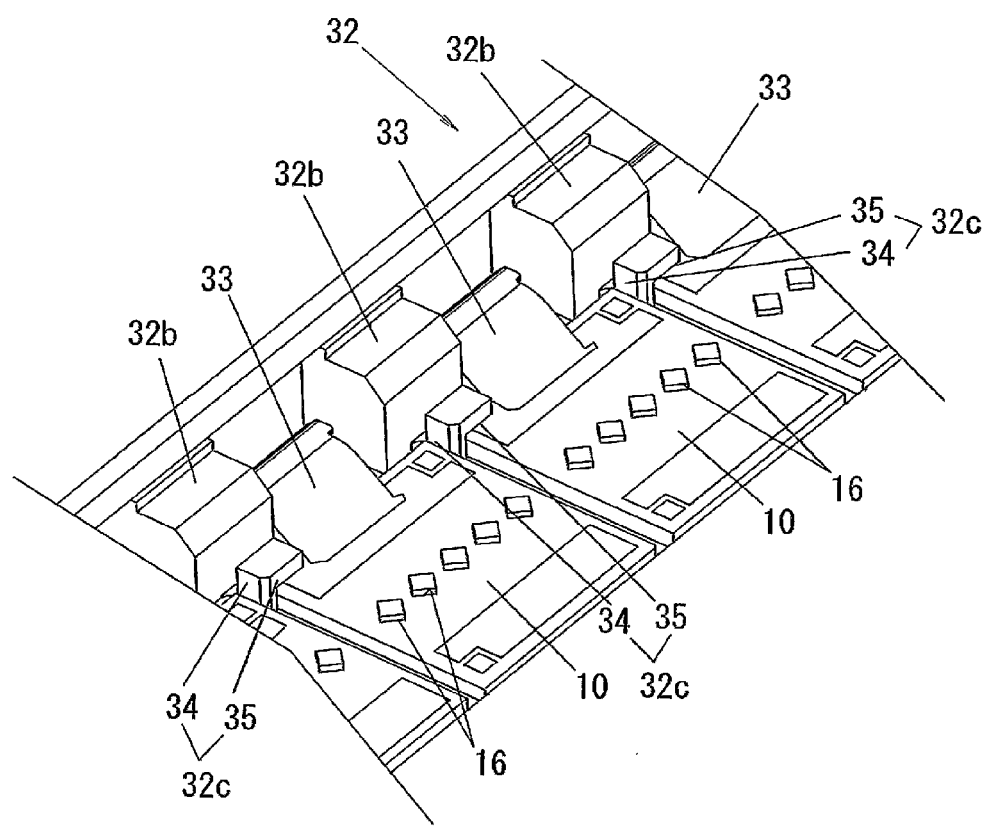
FIG. 5B is an expanded perspective view illustrating the essential parts of the fixation part.

First, as shown in FIGS. 4 and 5B, etc., each fixation part 32 has a retaining member 32a made of resin. The retaining member 32a is a long member extending in the disposal direction of the light source mounting substrates 10, and a plurality (for example, six) protrusions 32b are formed on the retaining member 32a at predetermined intervals in the lengthwise direction of the retaining member 32a. Among the six protrusions 32b, the protrusions 32b and 32b positioned on the left and right sides are formed to have a narrower width than the protrusions 32b positioned toward the center. Further, one of the protrusions 32b and 32b positioned on the left and right sides is formed to have a narrower width than the other protrusion 32b.

On the distal end of each protrusion 32b, a projection 32c having an L-shaped cross-section is formed integrally with the protrusion 32b, and one piece of the projection 32c (the piece that is orthogonal to the top surface of the light source mounting substrate 10) constitutes the restriction part 34.

One restriction part 34 abuts the side surface of one light source mounting substrate 10 to restrict the movement of the light source mounting substrate 10 in the lengthwise direction of the disposal groove 31. Thus, the restriction parts 34 are formed on only five of the protrusions 32b among the six protrusions 32b, and the protrusion 32b positioned at one end does not have a restriction part 34. A projection 32d is formed on this protrusion 32b positioned at one end, but the projection 32d does not constitute a restriction part 34. Rather, the projection 32d prevents deviation of the light source mounting substrate 10 disposed at the end of the disposal groove 31.

The float-up prevention parts 35 abut or approach an end on the top surface edge of the light source mounting substrates 10 disposed in the disposal groove 31, and prevents the light source mounting substrate 10 from floating up. Each float-up prevention part 35 is constituted by the other piece of the projection 32c (the piece that is parallel to the top surface of the light source mounting substrate 10).

The fixation parts 32 constituted as described above are provided as an opposing pair sandwiching the disposal groove 31. However, the opposing fixation parts 32 are disposed point symmetrically relative to the center of the disposal groove 31. Therefore, the float-up prevention parts 35 are disposed at diagonal corner portions on the top surface of each light source mounting substrate 10, thereby preventing the light source mounting substrate 10 from floating up.

The restriction parts 34 of one fixation part 32 abut one of the side surfaces of the light source mounting substrates 10, and the restriction parts 34 of the other fixation part 32 abut the other side surfaces of the light source mounting substrates 10 opposing the one side surfaces. Thereby, the restriction parts 34 restrict the movement of the light source mounting substrates 10 in the lengthwise direction of the disposal groove 31.

A base end of each fixation terminal 33 is interposed between the retaining member 32a of the fixation part 32 and the relay substrate 17, and the base end is sandwiched and retained by the retaining member 32a and the relay substrate 17. The relay substrate 17 and the fixation terminals 33 are electrically connected.

The pair of fixation parts 32 and 32 constituted as described above is disposed point symmetrically on the top surface of the base 71, and each fixation part 32 is fixed by screws or the like to the base 71. In the present example, the pair of fixation parts 32 and 32 is disposed point symmetrically, but the arrangement of the fixation parts 32 and 32 is not limited thereto, and the pair of fixation parts 32 and 32 can be disposed rotation symmetrically or in some other symmetrical shape.

If the fixation parts 32 are to be fixed to the base 71 by screws, means that prevents the fixation parts 32 from co-rotating with the screws is provided to the fixation parts 32 and the base 71.

Figure 7:
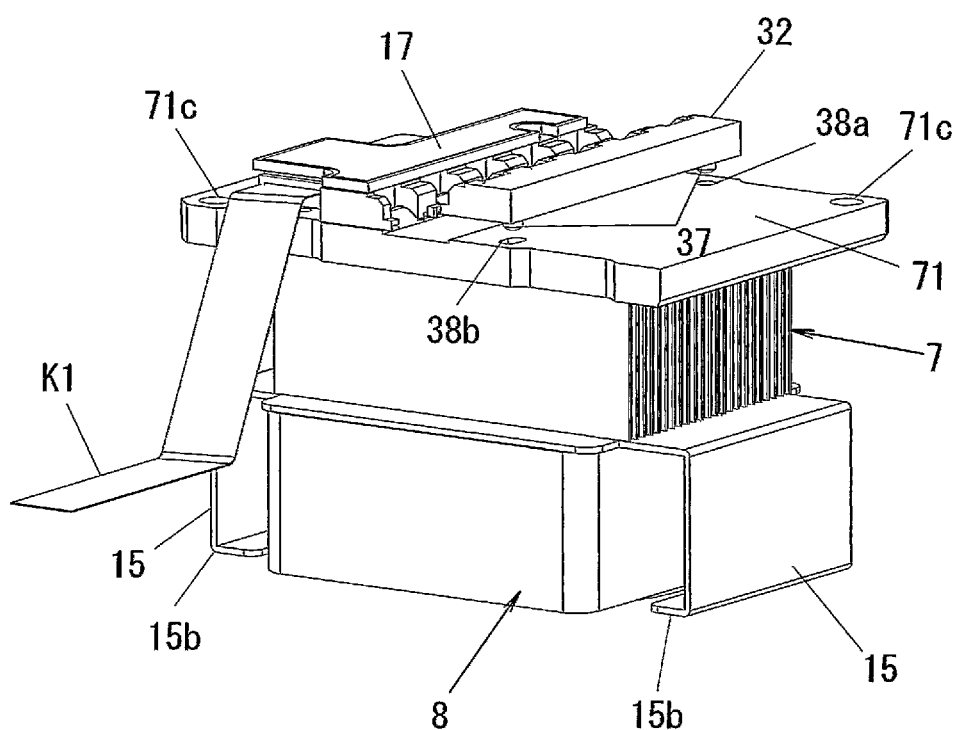
FIG. 7 is a perspective view of essential parts illustrating a base of the heat sink on which a recess is formed and a fixation part on which a protrusion is formed.

As shown in FIG. 7, a pair of protrusions 37 and 37 is formed spaced apart from each other in the lengthwise direction of the fixation part 32 on the bottom surface of each fixation part 32. The protrusions 37 are formed in an approximately cylindrical shape. In FIG. 7, the relay substrate 17 attached to the top surface of one of the fixation parts 32 has been omitted from the drawing.

On the other hand, as shown in FIG. 7 and FIG. 4, a pair of recesses 38a and 38b is formed on the top surface of the base 71. One recess 38a is a circular hole, and the other recess 38b is a long hole that is longer in the lengthwise direction of the disposal groove 31.

Each fixation part 32 engages with the base 71 in a protrusion-recess manner by engaging the protrusions 37 and 37 with the recesses 38a and 38b of the base 71.

In this way, in the case that a screw inserted into one end of the fixation part 32 is screwed into the base 71 before screwing a screw that is inserted into the other end of the fixation part 32 into the base 71, or one screw is loosened and removed from one end of the fixation part 32 in a state in which the other screw is removed from the other end of the fixation part 32, the fixation part 32 is prevented from co-rotating with a screw because the fixation part 32 is engaged with the base 71 in a protrusion-recess manner as described above. Therefore, the fixation part 32 does not collide with the light source mounting substrates 10, which are expensive.

By fixing the pair of fixation parts 32 and 32 to the base 71, the plurality of light source mounting substrates 10 are also fixed.

In other words, first, one fixation part 32 is disposed upon abutting the restriction parts 34 of this fixation part 32 to the side surfaces on one side of the light source mounting substrates 10, and then this fixation part 32 is fixed to the base 71 by screws.

Therein, the light source mounting substrates 10 are compressed and fixed to the bottom surface of the disposal groove 31 by the fixation terminals 33, and movement of the light source mounting substrates 10 in one direction of the lengthwise direction of the disposal groove 31 is restricted by the restriction parts 34.

Next, as shown in FIG. 6, the other fixation part 32 is fixed to the base 71 from the opposite side of the one fixation part 32 so as to sandwich the disposal groove 31.

In this case, this other fixation part 32 is disposed upon abutting the restriction parts 34 of this fixation part 32 to the side surfaces on the other side of the light source mounting substrates 10, and then this fixation part 32 is fixed to the base 71 by screws.

Therein, the light source mounting substrates 10 are compressed and fixed to the bottom surface of the disposal groove 31 by the fixation terminals 33, and movement of the light source mounting substrates 10 in the other direction of the lengthwise direction of the disposal groove 31 is restricted by the restriction parts 34.

In this way, the light source mounting substrates 10 disposed in the disposal groove 31 of the base 71 are positioned at predetermined intervals in the lengthwise direction of the disposal groove 31, and are fixed in the disposal groove 31 by the fixation parts 32 and 32. In this state, the float-up prevention parts 35 are disposed at diagonal corner portions on the top surface of each light source mounting substrate 10 and abut or approach these portions, thereby preventing the light source mounting substrate 10 from floating up.

Among the plurality of light source mounting substrates 10 that have been positioned and fixed, the light source mounting substrates 10 and 10 at both sides are positioned so as to leave a space toward the inside from the side surfaces (side surfaces in the longer dimension direction) of the base 71.

As shown in FIG. 1(b), a plurality (for example, six) of the light source units 6 constituted as described above are juxtaposed in a row left-to-right, thereby constituting the light source unit aggregate 3. The light source unit aggregate 3 is accommodated in the casing 2.

Figure 8:
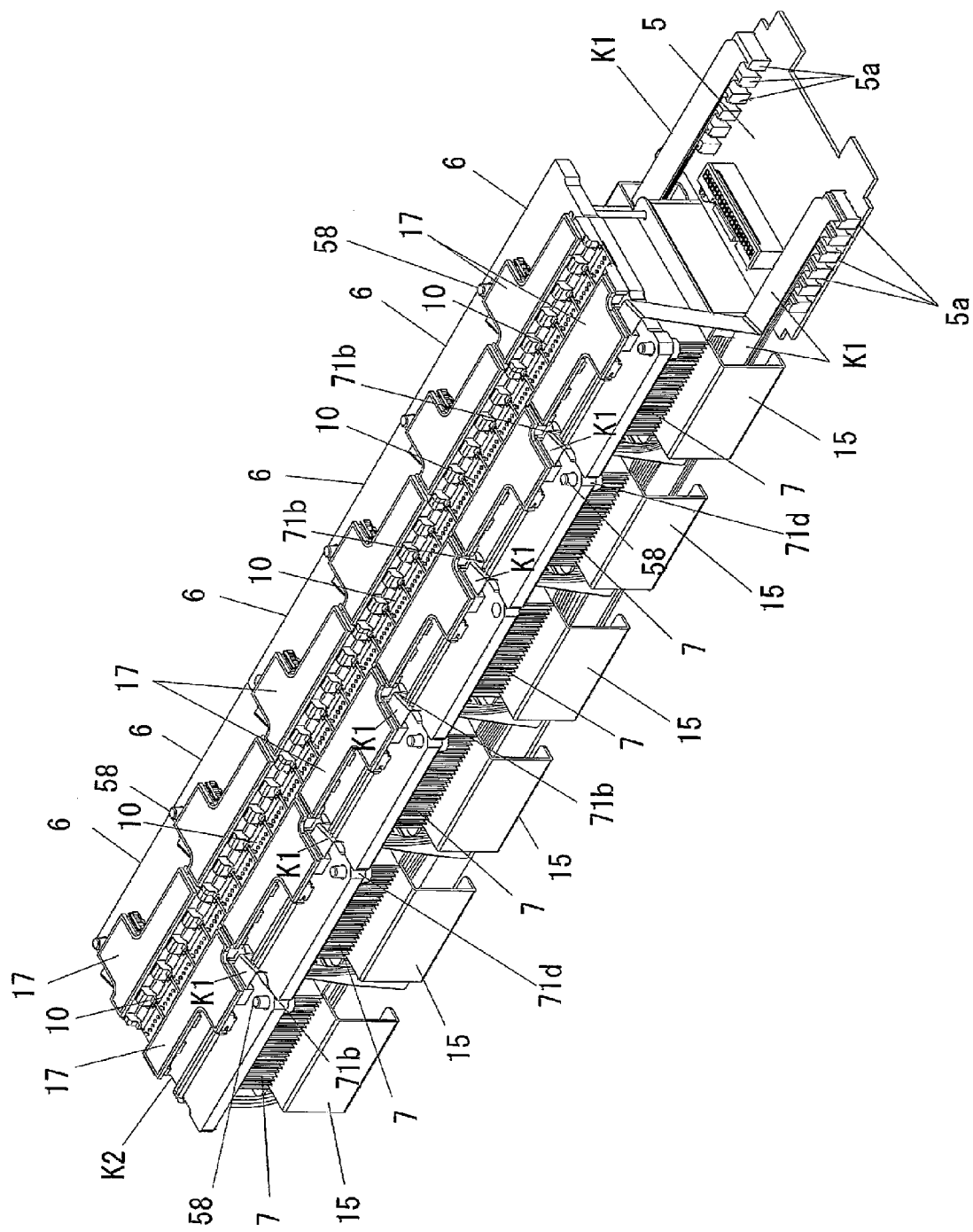
FIG. 8 is a perspective view illustrating a light source unit aggregate obtained by juxtaposing the light source units.

When juxtaposing the plurality of light source units 6 in a row in the casing 2, as shown in FIG. 8, the light source units 6 are juxtaposed so that the side surfaces along the longer dimension direction of the base 71 of adjacent light source units 6 are abutted to each other.

By juxtaposing the light source units 6 in a row as described above, the light source mounting substrate 10 positioned at the side surface of the base 71 of one light source unit 6 among two adjacent light source units 6 and 6 and the light source mounting substrate 10 positioned at the side surface of the base 71 of the other light source unit 6 are disposed with a predetermined interval therebetween.

Each cable K1 connected to the relay substrate 17 extends from the relay substrate 17 and crawls to the underside surface side of the base 71 through the cut-away portion (passing portion) 71b of the base 71, and then passes through the insertion part 15 to connect to the control substrate 5.

The cable K1 that is connected to the relay substrate 17 of the base 71 of the light source unit 6 that is positioned farthest away from the control substrate 5 first passes through the insertion part 15 of this light source unit 6. Next, the cable K1 successively passes through the insertion parts 15 of the other light source units 6, subsequently, the light source unit 6 that is positioned next farthest from the control substrate 5, and then connects to the control substrate 5.

Similarly, the cable K1 that is connected to the relay substrate 17 of the base 71 of the light source unit 6 that is positioned next farthest away from the control substrate 5 first passes through the insertion part 15 of this light source unit 6. Next, the cable K1 successively passes through the insertion parts 15 of the other light source units 6, subsequently, the light source unit 6 that is positioned next farthest from the control substrate 5, and then connects to the control substrate 5.

The control substrate 5 is a constant current substrate, and a plurality of connectors 5a are disposed in a row on the control substrate 5. Each connector 5a is connected to one of the cables K1. Since the control substrate 5 is a constant current substrate, it is not necessary to provide control resistors or the like to the light source units 6.

As shown in FIG. 1(b), a socket 5b that is electrically connected to the control substrate 5 is provided on the end frame 22 on which the control substrate 5 is provided, and a cable of an external power source is connected to the socket 5b.

As shown in FIG. 1(b) and FIGS. 9A to 11, the lens unit 4 has a frame 40 and a long rod-shaped rod lens 41 that is attached to the frame 40. Instead of the rod lens 41, a semicylinder-shaped cylindrical lens or a rectangular parallelepiped-shaped Fresnel lens may be used.

The frame 40 has a frame body 42 and side panels 43 and 44 attached to both ends of the frame body 42.

The frame body 42 is constituted by a pair of frame members 45 and 45. The side panels 43 and 44 are attached to both ends of the frame members 45 and 45. The frame members 45 and 45 are disposed with a predetermined interval therebetween, and thereby a penetrating part 42a that penetrates through the frame 40 from top to bottom along the lengthwise direction of the rod lens 41 is formed on the frame body 42.

Figure 11:
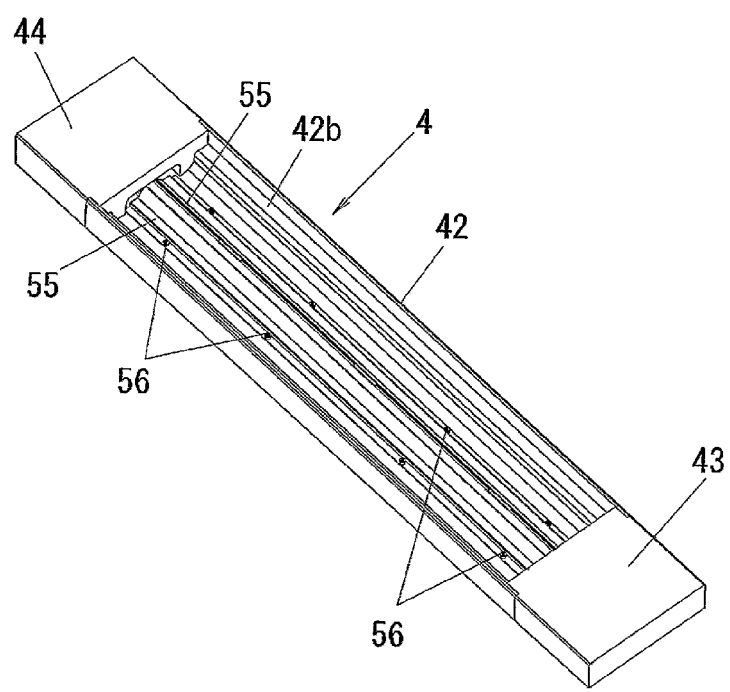
FIG. 11 shows a lens unit, and is a perspective view illustrating from the rear side a state in which light blocking plates are attached to the lens unit.

Disposal parts 46 are formed on the penetrating part 42a of the frame body 42. As shown in FIG. 11, the disposal parts 46 are formed by bending the edges opposing each other along the penetrating part 42a of the frame members 45 and 45 toward the inside (underside). Opposing disposal surfaces 46a and 46a of the disposal parts 46 that sandwich the penetrating part 42a are formed to be opened toward the inside (underside).

The rod lens 41 is disposed on the disposal surfaces 46a and 46a of the disposal parts 46 so as to face the penetrating part 42a from the underside of the frame body 42.

The rod lens 41 that is disposed on the disposal parts 46 as described above is fixed to the disposal parts 46 by fixation means 50.

As shown in FIG. 11, a plurality (for example, three) of the fixation means 50 are provided at predetermined intervals in the lengthwise direction of the rod lens 41. As shown in FIGS. 9 and 10, each fixation means 50 is constituted by a pair of fixation metal fittings 51 and 51 provided opposing each other so as to sandwich the penetrating part 42a. Each fixation metal fitting 51 has a fixed part 51a that is fixed to the underside surface of the frame body 42, and a support part 51b that stands up from the fixed part 51a and supports a portion of the peripheral surface of the rod lens 41.

The fixed parts 51a and 51a of the fixation metal fittings 51 and 51 are fixed to the underside surface of the frame body 42 by screws 52 so as to sandwich the penetrating part 42a therebetween. In this state, the support parts 51b and 51b are positioned on the penetrating part 42a side under the penetrating part 42a. The support parts 51b and 51b elastically compress a portion of the outer peripheral surface of the rod lens 41 that is disposed on the disposal parts 46. Thereby, the rod lens 41 is pressed to the disposal parts 46 and fixed to the disposal parts 46.

Figure 9A:
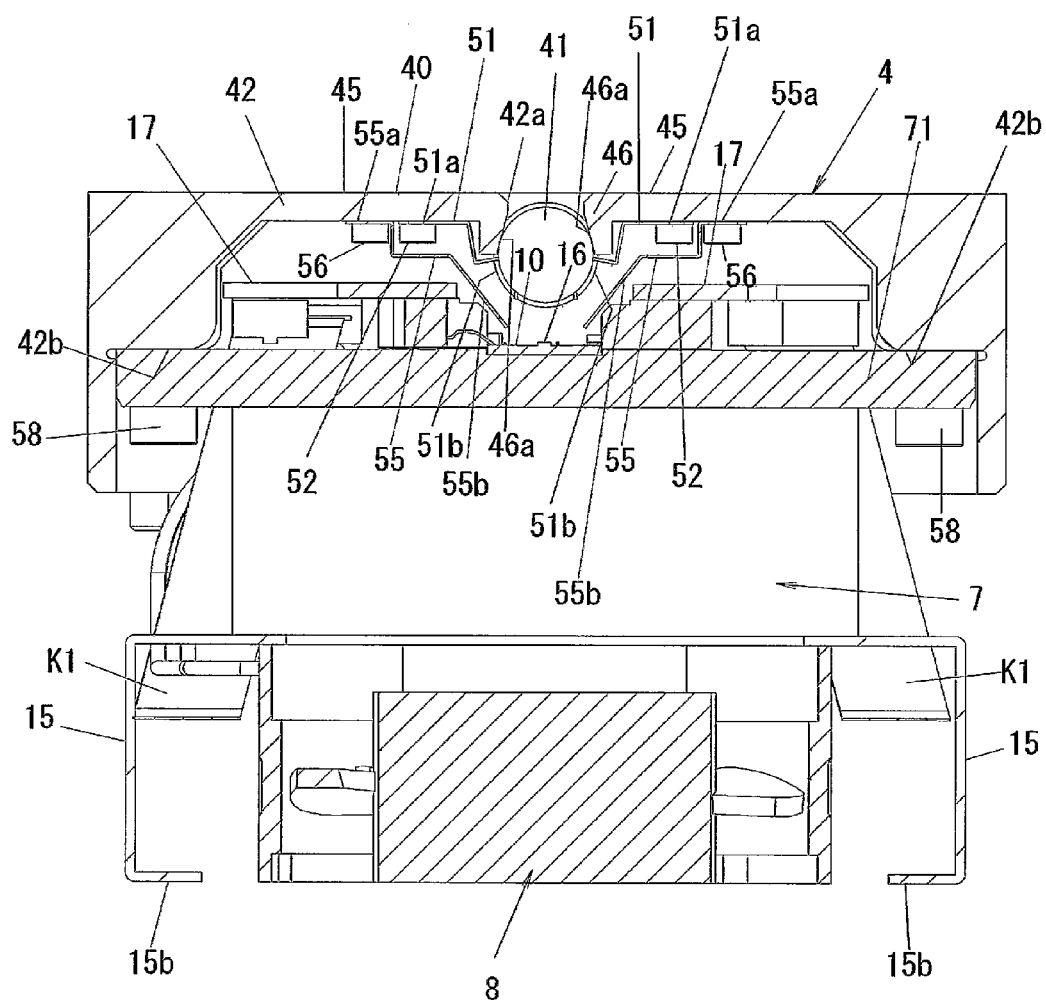
FIG. 9A is a transverse sectional view of the line light irradiation device.
Figure 10:
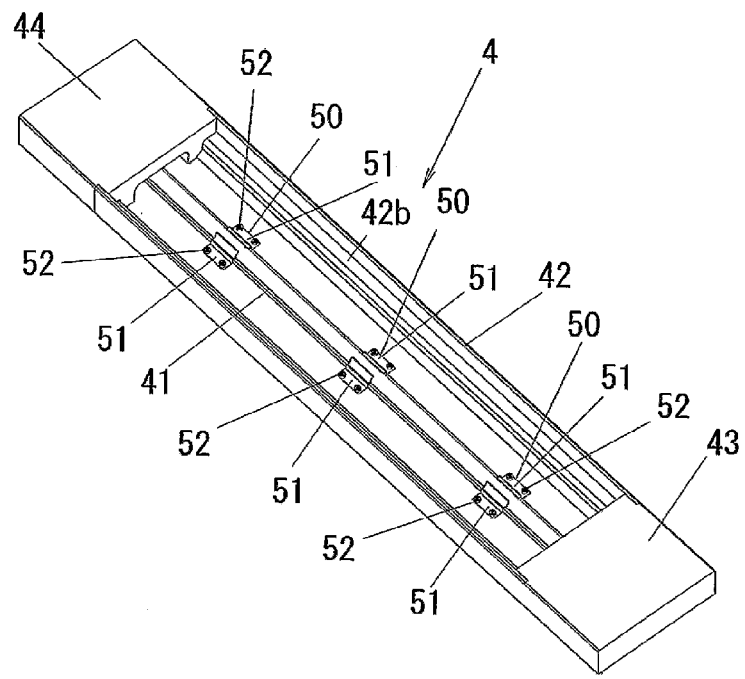
FIG. 10 shows a lens unit, and is a perspective view illustrating from the rear side a state in which a rod lens is attached to the lens unit.

As shown in FIGS. 9A and 11, light blocking plates 55 and 55 are attached on the underside surface of the frame body 42 so as to sandwich the penetrating part 42a therebetween.

Each light blocking plate 55 is formed as a long plate extending along the lengthwise direction of the rod lens 41, and includes a fixed part 55a that is fixed to the underside surface of the frame body 42 and a light blocking part 55b that is disposed standing up from the fixed part 55a between the rod lens 41 and the fixation part 32 and blocks light (ultraviolent radiation) irradiated toward the fixation part 32 side.

The fixed parts 55a and 55a of the light blocking plates 55 and 55 are fixed on the outside of the fixed parts 51a and 51a of the fixation metal fittings 51 and 51 to the underside surface of the frame body 42 by screws 56 so as to sandwich the penetrating part 42a therebetween. In this state, the light blocking parts 55b and 55b cover the fixation metal fittings 51 and 51, and are disposed between the rod lens 41 and the fixation parts 32. Thereby, the light blocking plates 55 and 55 block light (ultraviolet radiation) from the light sources 16 from being irradiated anywhere other than the rod lens 41 sides.

Figure 12:
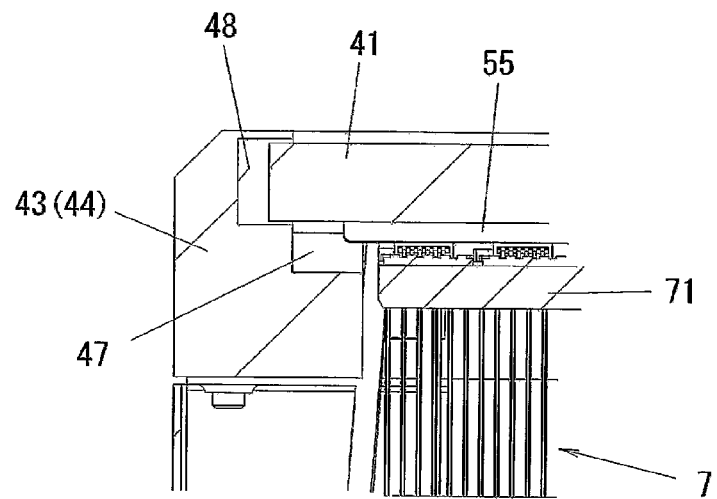
FIG. 12 is a sectional view of the essential parts on a rod lens end side illustrating a state in which another lens unit is attached to a casing.
Figure 13:
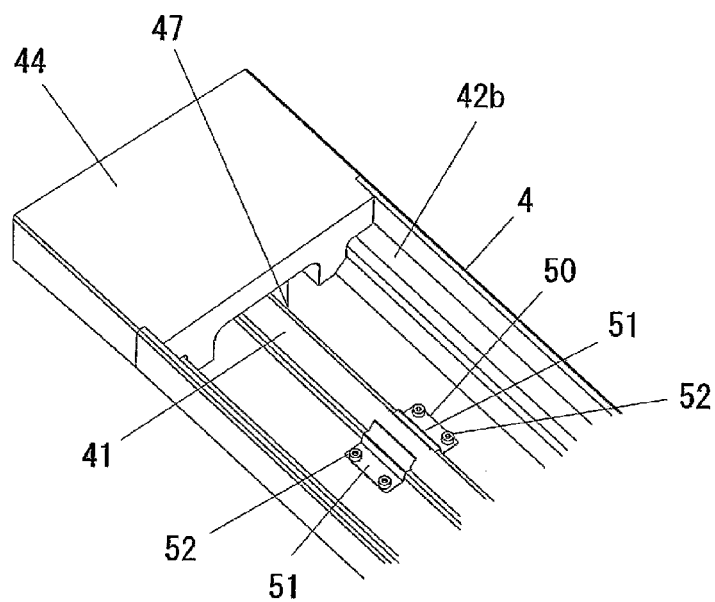
FIG. 13 shows another lens unit, and is a perspective view of the essential parts on one end of the rod lens.
Figure 14:
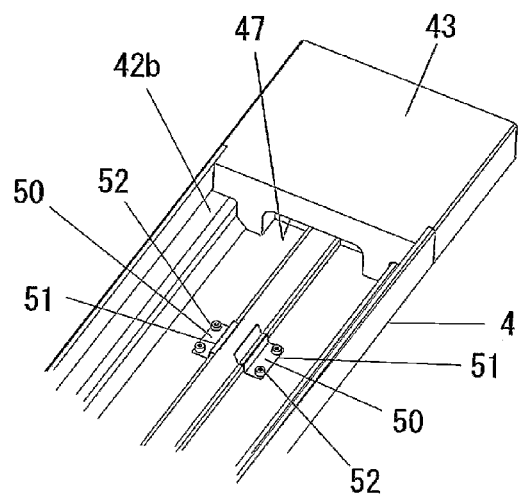
FIG. 14 shows another lens unit, and is a perspective view of the essential parts on the other end of the rod lens.

As shown in FIGS. 12 to 14, light blocking plate insertion recess 47 and 47 are formed opposing each other in the side panels 43 and 44 of the frame 40. Lens insertion recesses 48 and 48 are formed opposing each other in the bottom surfaces of the light blocking plate insertion recesses 47 and 47.

The ends of each light blocking plate 55 are inserted into the light blocking plate insertion recesses 47 and 47, and the light blocking plate insertion recesses 47 and 47 are formed in a substantially rectangular shape. The distance between the bottom surfaces of the light blocking plate insertion recesses 47 and 47 is longer than the length of the light blocking plates 55, and the distance between the opening edges of the light blocking plate insertion recesses 47 and 47 is shorter than the length of the light blocking plates 55.

Therefore, one end of each light blocking plate 55 is inserted into one of the light blocking plate insertion recesses 47, and then the light blocking plate 55 is moved toward the other light blocking plate insertion recess 47 side and the other end of the light blocking plate 55 is inserted into the other light blocking plate insertion recess 47. Thereby, the ends of the light blocking plate 55 are inserted respectively into the pair of light blocking plate insertion recesses 47 and 47.

The ends of the rod lens 41 are inserted into the lens insertion recesses 48 and 48, and the lens insertion recesses 48 and 48 are formed in a circular shape. The distance between the bottom surfaces of the lens insertion recesses 48 and 48 is longer than the length of the rod lens 41, and the distance between the opening edges of the lens insertion recesses 48 and 48 is shorter than the length of the rod lens 41.

Therefore, one end of the rod lens 41 is inserted into one of the lens insertion recesses 48, and then the rod lens 41 is moved toward the other lens insertion recess 48 side and the other end of the rod lens 41 is inserted into the other lens insertion recess 47. Thereby, the ends of the rod lens 41 are inserted respectively into the pair of lens insertion recesses 48 and 48.

In this way, by forming the lens insertion recesses 48 and 48 and the light blocking plate insertion recesses 47 and 47 in the frame 40, the rod lens 41 can be directly incorporated into the frame 40 from the underside surface side thereof. Therefore, the ease of incorporation of the rod lens 41 is improved.

Similarly, the ease of incorporation of the light blocking plates 55 is also improved. Further, since the ends of the light blocking plates 55 are inserted into the light blocking plate insertion recesses 47 and 47, the light blocking plates 55 and 55 can reliably block light from the light sources 16 from being irradiated anywhere other than the rod lens 41 side over the effective length of the rod lens 41 (the length between the side panels 43 and 44).

Figure 9B:
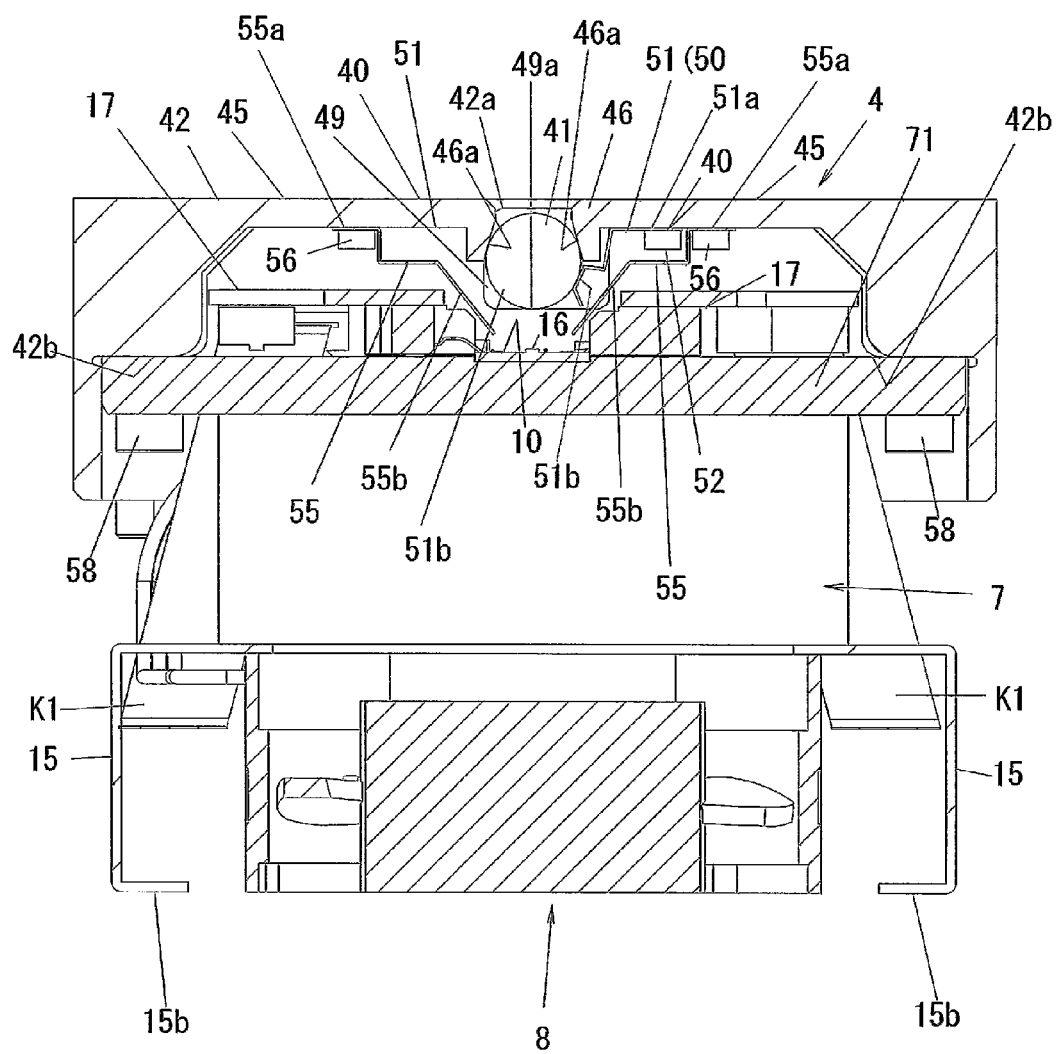
FIG. 9B is a transverse sectional view of another line light irradiation device.

As shown in FIG. 9B, the rod lens 41 can be fixed upon being positioned first. In other words, instead of the lens insertion recesses 48 and 48, lens insertion recesses 49 and 49 are formed opposing each other in the side panels 43 and 44. The lens insertion recesses 49 and 49 are formed in a quadrangle shape. Abutting parts 49a and 49a which are abutted by an area of the rod lens 41 that faces the underside surface side of the frame 40 are formed in the lens insertion recesses 49 and 49, and the abutting parts 49a and 49a function as fixation means.

The rod lens 41 is abutted to the abutting parts 49a and 49a and the disposal parts 46, and thereby the rod lens 41 is positioned in the top-to-bottom direction of the frame 40.

In the illustrated example, some portions on the outer peripheral surface of the rod lens 41 are also elastically compressed and fixed by the fixation metal fittings 51 provided on one side of the penetrating part 42a at predetermined intervals in the lengthwise direction of the rod lens 41. However, the fixation metal fittings 51 may be omitted.

According to this structure, the rod lens 41 is positioned in the top-to-bottom direction of the frame 40 by abutting the rod lens 41 to the abutting parts 49a and 49a and the disposal parts 46, and thus the distance between the rod lens 41 and the light sources 16 is fixed and light from the light sources 16 can be precisely converged.

Further, since the rod lens 41 is supported by the fixation metal fittings 51 between the abutting parts 49a and 49a, the rod lens 41 can be prevented from deflecting toward the light source 16 side.

As shown in FIGS. 9A and 11, abutting surfaces 42b and 42b, to which the bases 71 of the light source units 6 are abutted, are formed spaced apart from each other in parallel on the underside surface of the frame body 42. A plurality of screw holes are formed in the abutting surfaces 42b at predetermined intervals along the lengthwise direction of the abutting surfaces 42b.

As shown in FIG. 1 and FIG. 9, the lens unit 4 constituted as described above is placed on the casing 2, and the ends at the opening edges on the bottom surface of the lens unit 4 are disposed on the receiving surfaces 22d and 23d of the casing 2. The lens unit 4 is then fixed to the casing 2 by threading screws into the screw holes of the receiving surfaces 22d and 23d.

In this state, as shown in FIG. 1, in between the casing 2 and the lens unit 4, a long opening extending left-to-right is formed between the end frames 22 and 23, and the side surfaces of the heat sinks 7 (fins 72) which blow out air are facing the long opening.

The line light irradiation device 1 as described above is assembled, for example, as described below.

First, after assembling the lens unit 4, the lens unit 4 is placed on an assembly table (not illustrated) in a state in which the underside surface opening of the lens unit 4 is facing upwards.

Figure 15:
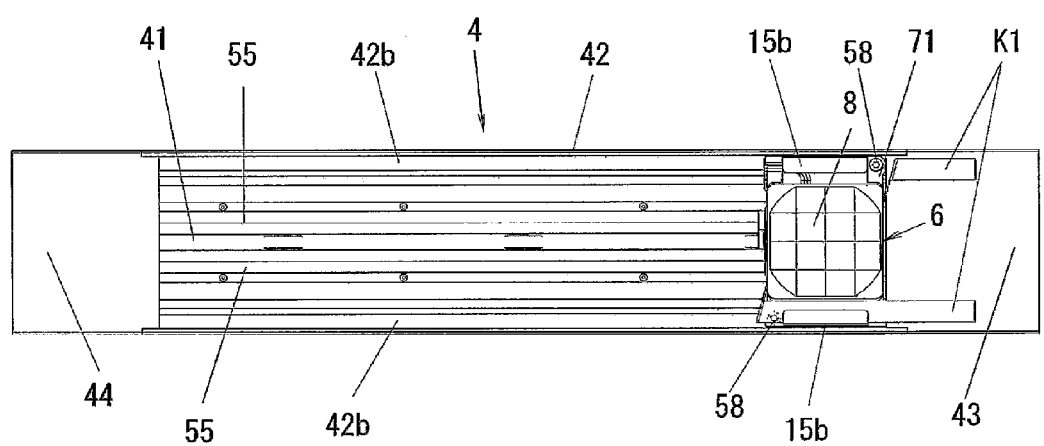
FIG. 15 is a bottom surface view illustrating a state in which one light source unit is disposed on the lens unit.

Next, as shown in FIG. 15, a first light source unit 6 is inserted into the lens unit 4 in a state in which the blower fan 8 is on the top side and the shorter dimension of the base 71 is facing the lengthwise direction of the lens unit 4. The base 71 is placed on the abutting surfaces 42b of the lens unit 4 and the side surface of the base 71 is abutted to the side panel 43. As shown in FIG. 1(b), the chamfered part 71d formed on the corner of the base 71 of the light source unit 6 is oriented to face the side panel 43 side and then the light source unit 6 is inserted into the lens unit 4. Subsequently, the cables K1 connected to the light source unit 6 are inserted into the insertion parts 15 and pulled to the side panel 43 side.

Figure 16:
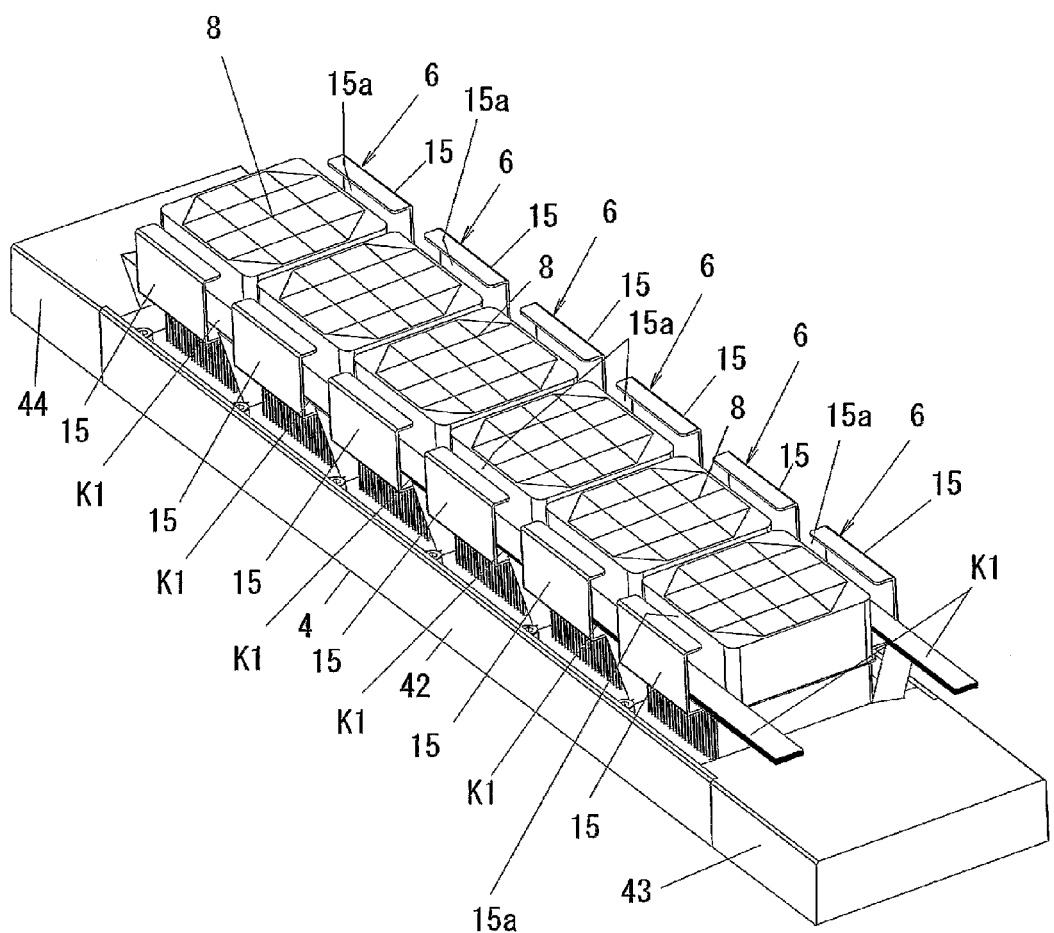
FIG. 16 is a perspective view illustrating a state in which six light source units are disposed on the lens unit.
Figure 17:
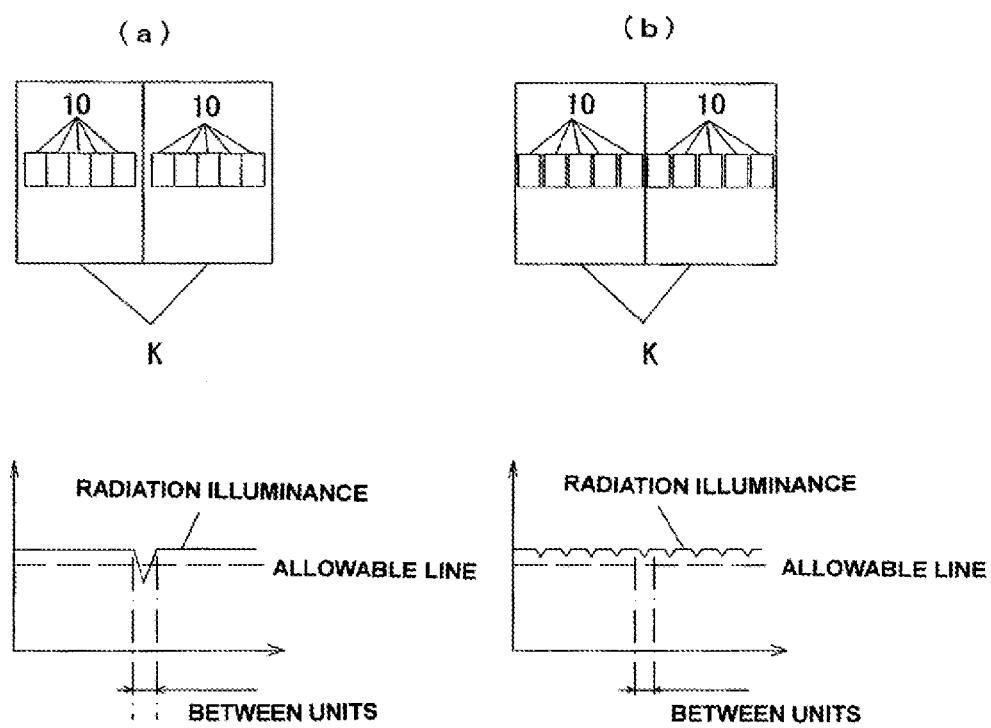
FIG. 17 are diagrams for explaining the radiation illuminance of alight source mounting substrate, and FIG. 17A explains the conventional radiation illuminance and FIG. 17B explains the radiation illuminance according to the present invention.

Next, as shown in FIG. 16, the second to sixth light source units 6 are successively inserted into the lens unit 4 in a state in which the blower fan 8 is on the top side and the shorter dimension of the base 71 is facing the lengthwise direction of the lens unit 4. The base 71 of each light unit 6 is placed on the abutting surfaces 42b of the lens unit 4 and the side surface of the base 71 of a subsequently inserted light source unit 6 is abutted to the side surface of the base 71 of the light source unit 6 that was previously inserted. As shown in FIG. 1(b), the chamfered part 71d formed on the corner of the base 71 of each light source unit 6 is oriented toward the side panel 43 side, and then each light source unit 6 is inserted into the lens unit 4 to form a single row in the juxtaposition direction of the light source units 6. Subsequently, the cables K1 connected to each light source unit 6 are inserted into the insertion parts 15 of that light source unit 6, and then inserted into the insertion parts 15 of the light source units 6 that have been previously inserted and finally pulled to the side panel 43 side.

When inserting the cables K1 into the insertion parts 15 of each light source unit 6, the cables K1 are inserted through the insertion openings 15a from a direction intersecting the lengthwise direction of the cables K1. Thereby, each cable K1 can be easily inserted into the insertion parts 15 of each light source unit 6.

The number of cables K1 inserted into each insertion part 15 decreases in order beginning with the light source unit 6 near the side panel 43. In other words, six cables K1 are inserted into the insertion parts 15 that are closest to the side panel 43, and one cable K1 is inserted into the insertion parts 15 that are farthest from the side panel 43. In the insertion parts 15 into which a plurality of cables K1 are inserted, the plurality of cables K1 are inserted in a state in which they are stacked on each other in the up-down direction as shown in FIGS. 8 and 1(b).

As shown in FIG. 2, the cables K1 pass from the light source mounting substrate 10 side of each light source unit 6 through the cut-away portions 71b formed on the base 71 and crawl to the underside surface side of the base 71 before being inserted into the insertion parts 15.

In this way, after inserting and accommodating the plurality (for example, six) of light source units 6 in the lens unit 4, bolts 58 are inserted into through-holes 71c formed at opposing corners of the base 71 and threaded into screw holes formed in the abutting surfaces 42b and 42b of the lens unit 4 to fix all of the light source units 6 to the lens unit 4.

Next, the casing 2 is attached to the lens unit 4 to which the light source units 6 have been fixed. In this case, the light source unit aggregate 3 consisting of six light source units 6 is inserted into the casing 2, and both ends on the left and right of the opening edges on the bottom surface of the lens unit 4 are disposed on the receiving surfaces 22d and 23d of the casing 2. Screws are then threaded into the receiving surfaces 22d and 23d to fix the light source unit aggregate 3 to the casing 2.

As shown in FIG. 1 (b), the cables K1 are pulled to the control substrate 5 provided within the end frame 22 and connected to the connectors 5a provided on the control substrate 5.

When connecting the cables K1 to the connectors 5a of the control substrate 5, for example, the end frame 22 in which the control substrate 5 is provided is removed from the side frames 21 and 21 and the cables K1 are pulled from between the ends of the side frames 21 and 21. The cables K1 are then connected to the connectors 5a, and then the end frame 22 is attached to the side frames 21 and 21.

According to the present embodiment, if a certain light source 16 in a certain light source unit 6 becomes defective, this light source unit 6 can be removed so as to exchange only the light source mounting substrate 10 on which the defective light source 16 is mounted, and it is not necessary to exchange the other light source mounting substrates 10 on which normal light sources 16 are mounted.

Therefore, as many normal light sources 16 as possible can be left as they are, and as a result, waste of the light sources 16 can be reduced. In addition, since the fixation of the light source mounting substrates 10 is achieved by compression by the fixation terminals 33, the light sources 16 can be easily exchanged.

Since a plurality of the light source mounting substrates 10 are positioned and fixed at predetermined intervals on the base 71 of the heat sink 7, dimensional errors do not accumulate at the juxtaposition ends, i.e. the sides on the top surface of the base 71, of the light source mounting substrates 10. Thus, the distance between the light source mounting substrates 10 and 10 between adjacent light source units 6 and 6 does not increase or decrease more or lower than a predetermined value, and this distance is kept within a predetermined tolerance. Accordingly, illuminance unevenness can be prevented between adjacent light source units 6 and 6.

The light source mounting substrates 10 that are on both sides among the plurality of light source mounting substrates 10 disposed on the base 71 are positioned so as to leave a space toward the inside from the side surfaces of the base 71. Also, the plurality of light source units 6 and 6 are juxtaposed in a state in which the side surfaces of the bases 71 are abutted to each other. Thereby, the light source mounting substrate 10 positioned at the side surface of the base 71 of one light source unit 6 among two adjacent light source units 6 and 6 and the light source mounting substrate 10 positioned at the side surface of the base 71 of the other light source unit 6 are disposed with a predetermined interval therebetween. Therefore, illuminance unevenness can be easily and reliably prevented between adjacent light source units 6 and 6.

In addition, an interval between the light source mounting substrate 10 positioned at the side surface of the base 71 among the plurality of light source mounting substrates 10 disposed on the base 71 and the side surface of the base 71 is set to ½ of the interval between adjacent light source mounting substrates 10 and 10 on the base 71. Therefore, the distance between the light source mounting substrates 10 and 10 positioned at opposing side surfaces of adjacent bases 71 and 71 is equal to the interval between adjacent light source mounting substrates 10 and 10 on the base 71. Thus, in the line light irradiation device including a plurality of the light source units 6, illuminance unevenness between adjacent light source mounting substrates 10 and 10 can be prevented and light can be more uniformly irradiated.

The positioning/fixation means 30 that positions and fixes the plurality of light source mounting substrates 10 has the disposal groove 31 formed on the base 71 and the fixation parts 32 that supply power to the light source mounting substrates 10 disposed in the disposal groove 31 and fix the light source mounting substrates 10 at predetermined intervals. Each fixation part 32 has the fixation terminals 33 and the restriction parts 34.

Therefore, the light source mounting substrates 10 can be positioned in a direction orthogonal to the disposal direction of the light source mounting substrates 10 by the disposal groove 31. Further, the restriction parts 34 abut the side surfaces of the light source mounting substrates 10, and thereby the light source mounting substrates 10 can be positioned in the lengthwise direction of the disposal groove 31.

In addition, the light source mounting substrates 10 are compressed and fixed to the bottom surface of the disposal groove 31 by the fixation terminals 33, and thereby the light source mounting substrates 10 that have been positioned can be fixed and power can be supplied to the light source mounting substrates 10.

The fixation parts 32 have the float-up prevention parts 35 that abut or approach an end on the top surface edge of each light source mounting substrate 10 to prevent the light source mounting substrate 10 from floating up. Therefore, the light source mounting substrates 10 can be prevented from floating up. Thus, the light source mounting substrates 10, which are expensive, can be prevented from deviating from the base 71 and becoming damaged or broken even if some of the fixation terminals 33 become broken during assembly or the like.

The two protrusions 37 are formed on each fixation part 32, and the two recesses 38a and 38b with which the protrusions 37 engage are formed on the top surface of the base 71, and each fixation part 32 engages with the base 71 in a protrusion-recess manner by the protrusions 37 and the recesses 38a and 38b. Therefore, when the plurality of light source mounting substrates 10 are fixed by the fixation parts 32 or the like, the fixation parts 32 can be prevented from rotating (co-rotating) with a screw in a plane parallel to the light source mounting substrates 10. Thus, the fixation parts 32 can be prevented from rotating and hitting the light source mounting substrates 10 and in turn scratching the light source mounting substrates 10 or causing them to deviate from the base 71.

The insertion parts 15 and 15 through which the cables K1 are passed are provided on the side parts of the blower fan 8, and each cable K1 passes from the light source mounting substrate 10 side and crawls to the underside surface side of the base 71 through the cut-away portion (passing portion) 71b of the base 71, and then passes through the insertion part 15 to connect to the control substrate 5. Therefore, the cables K1 do not need to be passed over the top of the light source mounting substrates 10. The top of the light source mounting substrates 10 is relatively high temperature due to the light sources 16, and thus if the cables K1 are passed over the top of the light source mounting substrates 10, the allowable current value may decrease due to the temperature. However, in the present embodiment, the cables K1 are passed through the insertion parts 15, and thus any decreases in the allowable current value due to the temperature can be suppressed.

The insertion parts 15 of the plurality of light source units 6 are continuous in the juxtaposition direction of the light source units 6, and the cables K1 are passed through these insertion parts 15. Further, the cables K1 are made of flexible flat cable (FFC), and thus the plurality of cables K1 can be easily bundled and connected to the control substrate 5. Even if the number of light source units 6 is increased, the cable laying process of the cables K1 is easy.

In addition, the plurality of light source units 6 are juxtaposed in a row and accommodated in the casing 2. Thus, the cables K1 connected to the light source mounting substrates 10 can pass between the cut-away portions 71b and 71b formed on adjacent light source units 6 and 6 and crawl to the underside surface side of the base 71. Thus, the cable laying process of the cables K1 is further facilitated.

Moreover, the cables K1 pass through the insertion parts 15, which are provided at positions avoiding the sides of the fins 72. Therefore, the flow of air that is blown out from the fins 72 is not obstructed by the cables K1.

Each insertion part 15 has the insertion opening 15a for inserting the cable K1 into the insertion part 15 from a direction intersecting the lengthwise direction of the cable K1. Thus, the cable K1 which has crawled to the underside surface side of the base 71 can be easily inserted from the insertion opening 15a and passed through the insertion part 15.

Further, each insertion part 15 has the deviation prevention part 15b that prevents deviation of the cable K1 that is inserted into the insertion part 15. Thus, the cable K1 that is inserted into the insertion part 15 can be prevented from deviating (for example, floating up or sagging down). Therefore, the cables K1 do not deviate and become an obstruction during the assembly of the line light irradiation device 1.

The fixation parts 32 are provided on the heat sink 7, and the relay substrates 17 connected to the plurality of light source mounting substrates 10 are provided on the fixation parts 32. The cables K1 are connected to the relay substrates 17. Therefore, the cables K1 do not have to be directly connected to the plurality of light source mounting substrates 10, and thus the cables K1 and the light source mounting substrates 10 can be easily connected. Also, power can be easily and reliably supplied from the control substrate 5 to the plurality of light source mounting substrates 10 via the cables K1 and the relay substrates 17.

Further, the cable K2 that supplies power to the blower fan 8 is connected to the relay substrate 17, and thus power can be supplied and control signals can be transmitted from the control substrate 5 to the blower fan 8 via the cable K1, the relay substrate 17, and the cable K2. Therefore, the cable K2 connected to the blower fan 8 does not have to be directly extended over to the control substrate 5, and thus the cable volume can be reduced.

The blower fan 8 is disposed on the inside of the base 71 of the heat sink 7 in a plan view. Thus, when juxtaposing the plurality of light source units 6, even if the adjacent bases 71 and 71 are abutted to each other, the blower fans 8 and 8 will not touch each other. Therefore, the plurality of light source units 6 can be easily juxtaposed, and since a predetermined gap exists between the adjacent blower fans 8 and 8, at least a certain amount of air can be supplied to the fins 72 side without the blower fans 8 having any difficulty in suctioning air.

The penetrating part 42a along the lengthwise direction of the rod lens 41 is formed in the frame 40 of the lens unit 4, and the disposal parts 46 on which the rod lens 41 is disposed are formed in the penetrating part 42a on the underside surface side of the frame 40. The rod lens 41 is disposed on the disposal parts 46 so as to face the penetrating part 42a from the underside surface side of the frame 40, and then the rod lens 41 is fixed to the disposal parts 46 by the fixation means 50.

Therefore, the rod lens 41 can be easily incorporated into the frame 40 from the underside thereof. Thus, the frame 40 can be assembled in advance and then the long rod-shaped rod lens 41 can be incorporated into the frame 40, and this facilitates the assembly of the lens unit 4.

Further, the pair of lens insertion recesses 48 and 48 is provided opposing each other in the frame 40. One end of the rod lens 41 is inserted into one of the lens insertion recesses 48, and then the rod lens 41 is moved toward the other lens insertion recess 48 side and the other end of the rod lens 41 is inserted into the other lens insertion recess 48. Thereby, the ends of the rod lens 41 are inserted respectively into the pair of lens insertion recesses 48 and 48. Thus, the long rod lens 41 can be more easily incorporated into the frame 40.

The light blocking plates 55 are attached to the frame 40. Thus, the light blocking plates 55 can block light (in the present embodiment, ultraviolet radiation) from the light sources 16 from being irradiated anywhere other than the rod lens 41 side. Therefore, such light is not irradiated on any members other than the rod lens 41 (for example, the resin portions of the fixation parts 32 or the relay substrates 17), and any defects which may be caused thereby can be prevented.

The pair of light blocking plate insertion recesses 47 and 47 is provided opposing each other on the frame 40. One end of the light blocking plate 55 is inserted into one of the light blocking plate insertion recesses 47, and then the light blocking plate 55 is moved toward the other light blocking plate insertion recess 47 side and the other end of the light blocking plate 55 is inserted into the other light blocking plate insertion recess 47. Thereby, the ends of the light blocking plate 55 are inserted respectively into the pair of light blocking plate insertion recesses 47 and 47, and thus the ends of the rod lens 41 that is positioned in the frame 40 can be reliably covered by the light blocking plates 55. Accordingly, the light blocking plates 55 and 55 can reliably block light from the light sources 16 from being irradiated anywhere other than the rod lens 41 side over the effective length of the rod lens 41.

In the present embodiment, as shown in FIG. 1(b), the control substrate 5 of the end frame 22 is disposed parallel to the lengthwise direction of the casing 2. However, the control substrate 5 may be provided perpendicular to the lengthwise direction of the casing 2. In this case, the connectors 5a provided on the control substrate 5 are disposed to as to face the light source unit 6 side. Thereby, the connectors 5a are aligned in a row in the stacking direction of the cables K1, and this is advantageous because the cables K1 can be easily connected to the connectors 5a.

REFERENCE SIGNS LIST 1 line light irradiation device
2 casing
4 lens unit
5 control substrate
6 light source unit
7 heat sink
8 blower fan
10 light source mounting substrate
15 insertion part
15a insertion opening
15b deviation prevention part
16 light source
17 relay substrate
30 positioning/fixation means (light source mounting substrate fixation means)
31 disposal groove
32 fixation part
33 fixation terminal
34 restriction part
35 float-up prevention part
37 protrusion
38 recess
40 frame
41 rod lens (lens)
42 frame body
42a penetrating part
46 disposal part
47 light blocking plate insertion recess
48 lens insertion recess
49a abutting part
50 fixation means (lens fixation means)
55 light blocking plate
71 base
71b cut-away portion (passing portion)
K1, K2 cable

The invention claimed is:
1. A line light irradiation device comprising:
   a light source mounting substrate on which a plurality of light sources are mounted in a row; and a light source unit on which a plurality of the light source mounting substrates are provided on a base in a row direction of the light sources,
wherein a plurality of the light source units are juxtaposed in the row direction of the light sources, and
the plurality of light source mounting substrates are fixed directly to the base by virtue of a fixation unit, the plurality of light source mounting substrates having fixed intervals therebetween.

2. The line light irradiation device according to claim 1, wherein
the light source mounting substrates that are on both sides among the plurality of light source mounting substrates disposed on the base are positioned so as to leave a space toward the inside from the side surfaces of the base, and
the plurality of light source units are juxtaposed in a state in which side surfaces of the bases are abutted to each other, and thereby the light source mounting substrate positioned at the side surface of the base of one light source unit among two adjacent light source units and the light source mounting substrate positioned at the side surface of the base of the other light source unit are disposed with a predetermined interval therebetween.

3. The line light irradiation device according to claim 1, wherein
the fixation unit comprises a fixation part that supplies power to each light source mounting substrate disposed on the base and fixes the light source mounting substrate, and
the fixation part comprises a fixation terminal that supplies power to the light source mounting substrate and compresses and fixes the light source mounting substrate to the base.

4. The line light irradiation device according to claim 3, wherein the fixation unit comprises a disposal groove that is formed on the base and restricts movement of each light source mounting substrate disposed on the base in a direction orthogonal to a disposal direction of the light source mounting substrate.

5. The line light irradiation device according to claim 3, wherein the fixation part comprises a float-up prevention part that abuts or approaches an upper surface edge of each light source mounting substrate and prevents the light source mounting substrate from floating up.

6. The line light irradiation device according to claim 2, wherein an interval between the light source mounting substrate positioned at the side surface of the base among the plurality of light source mounting substrates disposed on the base and the side surface of the base is ½ of an interval between adjacent light source mounting substrates on the base.

7. The line light irradiation device according to claim 3, wherein
the fixation part is provided on both sides of the light source mounting substrates so as to form a pair of fixation parts sandwiching the light source mounting substrates, and each fixation part has a plurality of the fixation terminals, and
one side of each of the plurality of light source mounting substrates is fixed to the base by the fixation terminals of one of the fixation parts, and the other side of each of the plurality of light source mounting substrates is fixed to the base by the fixation terminals of the other fixation part.

8. The line light irradiation device according to claim 3, wherein the fixation part comprises a restriction part that abuts the side surface of each light source mounting substrate to restrict movement of the light source mounting substrate in the disposal direction of the light source mounting substrate.

9. The line light irradiation device according to claim 3, wherein
a protrusion is formed on one of the fixation part or the base, and a recess with which the protrusion engages is formed on the other of the fixation part or the base, and
the fixation part engages with the base in a protrusion-recess manner via the protrusion and recess.

\* \* \* \* \*